US012788618B2

(12) United States Patent
Lee, Jr.

(10) Patent No.: US 12,788,618 B2
(45) Date of Patent: Nov. 10, 2026

(54) MANDIBULAR ADVANCEMENT DEVICE FOR FACILITATING CIRCUMDUCTION OF THE MANDIBLE

(71) Applicant: Randy Lee, Jr., Albuquerque, NM (US)

(72) Inventor: Randy Lee, Jr., Albuquerque, NM (US)

( * ) Notice: Subject to any disclaimer, the term of this patent is extended or adjusted under 35 U.S.C. 154(b) by 0 days.

(21) Appl. No.: 18/976,389

(22) Filed: Dec. 11, 2024

(65) Prior Publication Data

US 2025/0186247 A1 Jun. 12, 2025

Related U.S. Application Data

(60) Provisional application No. 63/608,314, filed on Dec. 11, 2023.

(51) Int. Cl.
*A61F 5/56* (2006.01)
*A61C 7/08* (2006.01)

(52) U.S. Cl.
CPC ................ *A61F 5/566* (2013.01); *A61C 7/08* (2013.01)

(58) Field of Classification Search
CPC ...... A61F 5/56; A61F 5/566; A61F 2005/563; A61C 5/90; A61C 7/06; A61C 7/08; A61C 7/10; A61C 7/36; Y10S 602/902; A63B 2071/086
See application file for complete search history.

(56) References Cited

U.S. PATENT DOCUMENTS 11,311,407 B1 * 4/2022 Fallon ..................... A61F 5/566
2011/0017220 A1 1/2011 Lindsay et al.
2018/0153643 A1 6/2018 Lambert
2020/0268546 A1 * 8/2020 Radmand ................ A61F 5/566
2023/0086923 A1 3/2023 Leblanc et al.

* cited by examiner

*Primary Examiner* — Alireza Nia
*Assistant Examiner* — Andrew Jun-Wai Mok
(74) *Attorney, Agent, or Firm* — Ashok Tankha

(57) ABSTRACT

A mandibular advancement device (MAD) facilitating protrusion, retraction, translation, and rotation of a mandible is provided. The MAD comprises a fit connector, and left and right bite tray assemblies. Each bite tray assembly, mirror images of each other, comprise top and bottom bite plates, hinge plate, pin, and circumduction anchor rod. The top and bottom bite plates cradle upper and lower teeth respectively, while the hinge plate facilitates mouth opening and closing via a pin connection to the top bite plate and secure yet mobile connections to the bottom bite plate via the circumduction anchor rod. This rod, insertable into elliptical cylinder holes and semi-cylindrical depressions, allows lateral translation and rotation between connected parts. The hinge plate incorporates a flexible member for mandible protrusion and retraction, teeth-like structures to maintain minimum advancement, and a tension prong for stable fit. Adjustable-length circumduction anchor rods cater to varying mandibular advancement needs.

21 Claims, 35 Drawing Sheets

MANDIBULAR ADVANCEMENT DEVICE FOR FACILITATING CIRCUMDUCTION OF THE MANDIBLE

CROSS-REFERENCE TO RELATED APPLICATIONS

This application claims priority to and the benefit of the provisional patent application titled "Mandibular Advancement Device", application No. 63/608,314, filed in the United States Patent and Trademark Office on Dec. 11, 2023. The specification of the above referenced patent application is incorporated herein by reference in its entirety.

BACKGROUND

Mandibular advancement devices (MADs) generally work by using the teeth as a contact point, both as an anchor and a lever, to move the mandible forward. This is typically done by having an offset mechanism that allows the MAD to advance the mandible by pushing the lower jaw forward, thereby putting forward pressure on the teeth of the lower jaw, while simultaneously anchoring on the upper jaw, which places backward pressure on the teeth of the upper jaw. Since MADs are made to be used when the user sleeps, these pressures are applied over a long period of time. The jaw also moves during sleep, thus changing the position of the teeth several times during a sleep session.

With the current MADs available, teeth discomfort, teeth pain, forward dental drift of the lower teeth, and backward dental drift of the upper teeth are all common occurrences with usage. The main reason for this is that the MAD is using the teeth as a lever but is unable to move with the teeth when the jaw changes position. This causes the MAD to slip toward the end of the teeth, greatly increasing the pressure on them, as it changes the force applied from a straight forward or backward pressure to more of a forward or backward rotational pressure on the teeth; the rotational movement is the teeth rotating at their root insertion point. That is, if the MAD does not slip off the teeth entirely and cease to function, which they often do.

While there are a few MADs on the market, none of the MADs currently available move with the mandible. While most MADs don't move at all, those that do only open and close, and they do so in ways that don't allow the MAD to move as the mandible moves. The mandible naturally does not move in just one direction. As the mandible opens, it also tracks forward. Unless a MAD can open while also moving in forward traction, it will not be able to move with the teeth, causing the MAD to slip off. Likewise, when the mandible translates from side to side, the mandible does so with a slight amount of rotation as well. Unless a device can translate and compensate for that rotation as the mandible does so, the MAD again won't be able to move with the teeth, and this will eventually cause the MAD to slip off.

Allowing circumduction helps the mandibular advancement device (MAD) fit more comfortably by mimicking the natural movement of the mandible. If the device were to rigidly hold the mandible in one fixed position, it may result in discomfort, soreness, or even jaw pain over time to the user. A device that respects the mandible's natural mobility can reduce the risk of these issues, making it more likely that the user will wear the device consistently. Moreover, the mandible is not meant to stay in one fixed position for prolonged periods. By permitting circumduction, the MAD helps avoid unnecessary strain on the jaw joints and muscles. Restricting jaw movement could contribute to temporomandibular joint (TMJ) dysfunction or other musculoskeletal problems. A device that allows slight movement can minimize these risks.

During sleep, people often change positions, and the mandible moves in response to the new head or body posture. A MAD that allows circumduction enables the mandible to adjust to these position changes without forcing it into an unnatural alignment. This flexibility helps the device remain effective in maintaining airway patency, i.e., keeping the airway open, regardless of how the user sleeps, whether on their back, side, or stomach. Furthermore, circumduction facilitates natural mouth movements like swallowing or slight jaw adjustments during breathing. A device that allows for these movements is more likely to be well-tolerated throughout the night, leading to better compliance and improved sleep quality.

Hence, there is a need for a mandibular advancement device (MAD) that does not place undue pressure on the teeth leading to discomfort, pain, and dental drift. Moreover, there is a need for a MAD that moves as the mandible moves, facilitating simultaneous opening and closing, protrusion and retraction, and side-to-side and/or lateral translation and rotation of the mandible. Furthermore, there is a need for a MAD that stays with the mandible and does not slip off the teeth, making for a much more comfortable, effective, and enjoyable user experience.

SUMMARY OF THE INVENTION

The mandibular advancement device (MAD) disclosed herein addresses the above-recited need for reliable and comfortable mandibular advancement for treating obstructive sleep apnea, snoring, and teeth grinding while facilitating circumduction, including opening and closing, protrusion and retraction, and side-to-side or lateral translation and rotation, of the mandible without placing undue pressure on the teeth and causing oral issues. The MAD disclosed herein has a split design, allowing the right and left sides of the device to move independently. The split design has less surface area. Therefore, the MAD disclosed herein will feel smaller than existing mandibular advancement devices, while being more comfortable in general, exerting less pressure on the teeth and causing less teeth drift. Moreover, the MAD disclosed herein has an adjustable fitting connector, which coupled with the split design, will allow for usage of the MAD disclosed herein for a varying amount of mouth sizes and widths.

The mandibular advancement device (MAD) disclosed herein provides an adjustable amount of mandibular advancement and a custom moldable dental bite plate insert. The MAD moves as the mandible moves, providing four modes of active movement. The MAD opens and closes with the mouth. Furthermore, the MAD moves in translation (side to side) with the mandible. The MAD also moves in rotation with the mandible while translating. Moreover, the MAD moves in traction and retraction, i.e., forward and backward, while advancing the mandible. The MAD has two articulation joints to achieve the open, close, and side to side movement, while also having a translating and rotating articulation to help facilitate the translation and subsequent rotational movement of the mandible. Furthermore, the MAD has a flexible member that allows for protrusion and retraction of the mandible. Since the MAD stays with the mandible, it does not slip off the teeth.

The mandibular advancement device (MAD) disclosed herein comprises a fit connector, a left bite tray assembly, and a right bite tray assembly. Each of the left and the right bite tray assemblies comprise a top bite plate, a bottom bite plate, a hinge plate, a pin, and a circumduction anchor rod. The top bite plate, the bottom bite plate, and the hinge plate of the left and the right bite tray assemblies are laterally inverted mirror images of each other. The top bite plate fits around a portion of the upper teeth and the bottom bite plate fits around a portion of the lower teeth. The hinge plate is connected to the top bite plate via the pin that allows for relative rotation between the top bite plate and the hinge plate around the pin to facilitate opening and closing of the mouth while the MAD is in use. The hinge plate is connected to the bottom bite plate via the circumduction anchor rod, which has a cuboidal section that is inserted into a hole in the shape of an elliptical cylinder in the bottom bite plate and a semi-cylindrical section that is inserted into a semi-cylindrical-shaped depression in the hinge plate. The connection between the circumduction anchor rod and the bottom bite plate is secure and allows lateral translation and rotation between them. The connection between the circumduction anchor rod and the hinge plate is secure and allows lateral translation between the hinge plate and the bottom bite plate. The articulations between the top bite plate and the hinge plate and between the hinge plate and the bottom bite plate facilitate lateral translation and rotation of the mandible while the MAD is in use.

The hinge plate has a flexible member that extends and contracts facilitating protrusion and retraction of the mandible associated with opening and closing of the mouth respectively. Moreover, the hinge plate has a teeth-like structure that maintains a minimum advancement of the mandible during retraction of the mandible. Furthermore, the hinge plate has a tension prong that provides tension when opening the mouth for enabling a stable fit of the mandibular advancement device (MAD) in the mouth. Furthermore, the circumduction anchor rod has different embodiments varying in length to accommodate a required level of mandibular advancement.

The top and the bottom bite plates have enclosures. The enclosures of the top and the bottom bite plates each securely house a moldable bite insert. When fitting the mandibular advancement device (MAD) to the mouth for the first time, the left and the right bite tray assemblies are attached to the fit connector using capital-H-shaped connectors in the fit connector, substantially preventing movement of the MAD. This assembly is then connected to a Y-shaped connector in the fit connector. The fit connector is adjusted according to the required width to fit the MAD to the mouth by sliding the capital-H-shaped connectors along guiding slots in the arms of the Y-shaped connector. After fitting the MAD in the mouth, the MAD is heated in boiling water and bitten for the moldable bite inserts to conform to the teeth surrounded by the MAD. The fit connector is then removed and the left and the right bite tray assemblies are used independently without the fit connector during regular use of the MAD, wherein the MAD facilitates protrusion, retraction, translation, and rotation of the mandible while advancing the mandible.

These and further features of the present invention will be apparent with reference to the following description and drawings. In the description and drawings, particular embodiments of the invention have been disclosed in detail as being indicative of some of the ways in which the principles of the invention may be employed, but the invention is not limited correspondingly in scope. Rather, the invention includes all changes, modifications and equivalents coming within the spirit and terms of the claims.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

The foregoing summary, as well as the following detailed description of the invention, is better understood when read in conjunction with the appended drawings. For illustrating the embodiments herein, exemplary constructions of the embodiments are shown in the drawings. However, the embodiments herein are not limited to the specific components, modules, and methods disclosed herein. The description of a component, or a module, or a method step referenced by a numeral in a drawing is applicable to the description of that component, or that module, or that method step shown by that same numeral in any subsequent drawing herein.

DETAILED DESCRIPTION OF THE INVENTION

Disclosed herein is a mandibular advancement device facilitating circumduction of the mandible. A mandibular adjustment device is an oral device designed to help users who suffer from obstructive sleep apnea and loud snoring. Obstructive sleep apnea occurs when the upper airway becomes partially or completely blocked during sleep, which can disrupt breathing and lead to poor sleep quality. The soft tissues in the throat collapse, causing pauses in breathing, known as apneas, or shallow breaths, known as hypopneas. This condition can lead to various health issues over time, such as problems with circulation, the nervous system, and even daytime fatigue, irritability, and headaches.

The primary goal of a mandibular advancement device is to improve sleep quality by reducing or eliminating snoring and breathing interruptions. This is achieved by repositioning the mandible, that is, the lower jaw, slightly forward. When the jaw is advanced, it helps to open the airway, particularly in the area of the throat where airway collapse tends to occur. This repositioning not only helps stabilize the jaw but also affects other structures in the throat, such as the hyoid bone, a bone that supports the tongue, preventing them from shifting backward and blocking the airway.

By adjusting the position of the jaw and hyoid bone, the mandibular advancement device reduces the narrowing of the pharyngeal space, where snoring and airway blockages commonly happen. It causes a slight forward movement of the tongue and soft palate, which increases the size of the airway, especially in its lateral dimensions, that is, the sides of the throat. As a result, the airway becomes less likely to collapse during sleep, leading to a reduction in snoring and a decrease in the frequency of apneas and hypopneas.

Circumduction refers to the ability of the mandible to move in a circular or semi-circular motion. This movement involves the jaw being able to rotate and shift both horizontally and vertically. In a healthy, non-restricted jaw, circumduction allows the mouth to open, close, and shift sideways, accommodating various functions such as talking, chewing, and even adjusting head position during sleep. For a mandibular advancement device to be effective and comfortable, it's important that it allows for some degree of circumduction of the mandible to ensure that the device does not restrict normal jaw movement during sleep.

Figure 1:
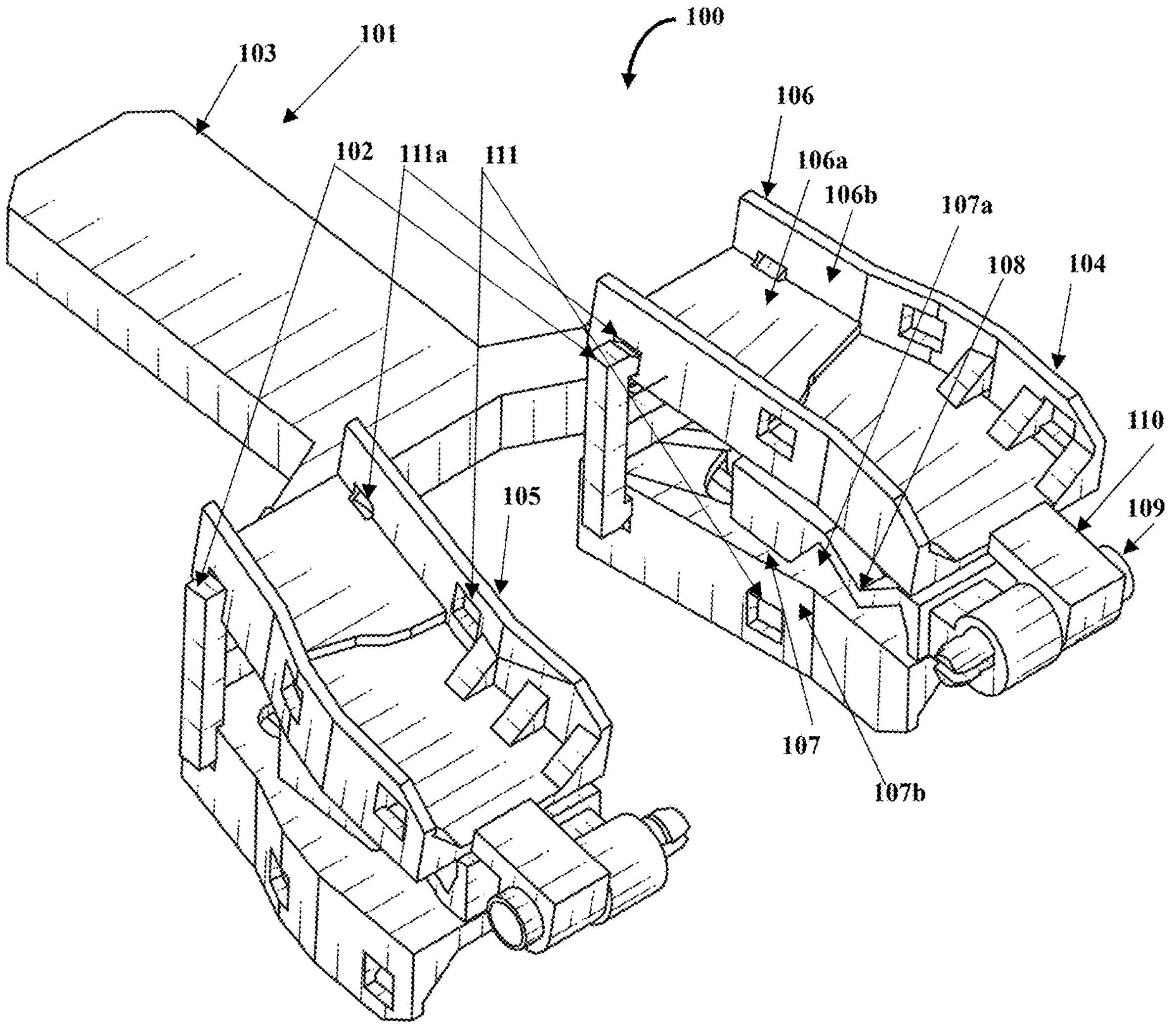
FIG. 1 illustrates a perspective view of a mandibular advancement device.
Figure 7A:
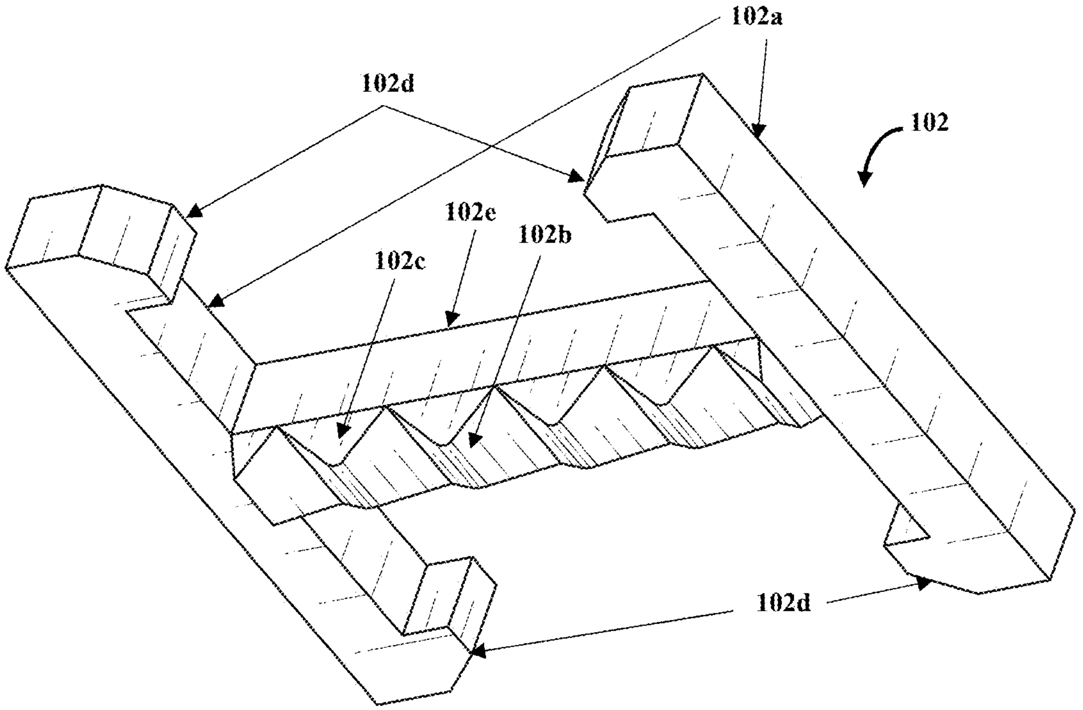
FIGS. 7A-7B illustrate perspective views of a H connector of the mandibular advancement device.
Figure 8A:
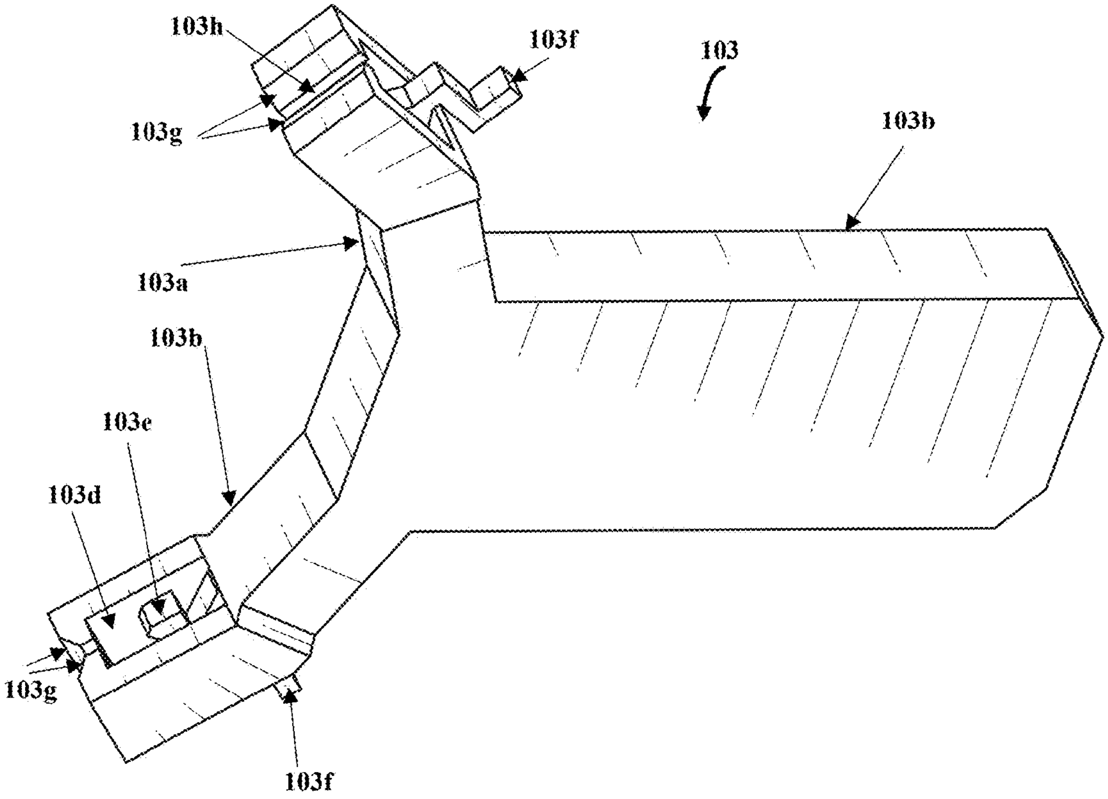
FIGS. 8A-8C illustrate perspective views of a Y connector of the mandibular advancement device.

FIG. 1 illustrates a perspective view of a mandibular advancement device 100. The mandibular advancement device (MAD) 100 comprises a fit connector 101, a left bite tray assembly 104, and a right bite tray assembly 105. The fit connector 101 is used to align the left bite tray assembly 104 and the right bite tray assembly 105 in the mouth of a user of the MAD 100. In an embodiment, the fit connector 101 is used for alignment only during the first time, and is adjustable to ensure a fit in mouths of different sizes of users. Thereafter, the fit connector 101 remains detached and only the left and the right bite assemblies 104 and 105 are worn by the user. The fit connector 101 comprises a pair of H connectors 102 and a Y connector 103. Each of the H connectors 102 is shaped in the form of a capital letter 'H' and comprises two vertical strokes and a crossbar 102*e*, as shown in FIG. 7A. The Y connector 103 is shaped in the form of a capital letter 'Y' and comprises two arms 103*a* and 103*b*, and a stem 103*c*, as shown in FIG. 8A. Each arm 103*a* and 103*b* of the Y connector 103 has a guide slot 103*d* at its end into which the crossbar 102*e* of one of the H connectors 102 is slid to detachably attach the H connectors 102 to the Y connector 103. The left bite tray assembly 104 is detachably attached to one of the H connectors 102 and the right bite tray assembly 105 to the other. The H connectors 102 can be individually adjusted by moving the crossbars 102*e* side to side along the guide slots 103*d* of the arms 103*a* and 103*b* of the Y connector 103 to accommodate mouths of different widths when the MAD 100 is being fitted to the mouth of the user. To fit the MAD 100 in the mouth of the user, the user holds the Y connector 103 by its stem 103*c* and places the attached left and right bite tray assemblies 104 and 105 onto the teeth in the mouth of the user. The fit connector 101 prevents movement of the left and the right bite tray assemblies 104 and 105 in any direction to obtain an accurate fit.

Each of the left bite tray assembly 104 and the right bite tray assembly 105 comprises a top bite plate 106, a bottom bite plate 107, a hinge plate 108, a pin 109, and a circumduction anchor rod 601, shown in FIGS. 1, and 6A-6H. The top bite plate 106, shown in FIGS. 1, 4A and 4H, fits around a portion of the upper teeth of the user of the MAD 100 and comprises a top enclosure 106*a* for accommodating a moldable bite insert 1601, shown in FIG. 16B, a top connector section 106*b*, and the first part 106*c* of two parts of a hinge pin receptacle 110. The bottom bite plate 107 fits around a portion of the lower teeth of the user of the MAD 100 and comprises a bottom enclosure 107*a*, shown in FIGS. 1, 2A and 2B, for a moldable bite insert 1601, a bottom connector section 107*b*, and an anchor bottom receptacle 107*c*, shown in FIG. 2B. The top bite plate 106, the bottom bite plate 107, and the hinge plate 108 of the right bite tray assembly 105 are laterally inverted mirror images of the top bite plate 106, the bottom bite plate 107, and the hinge plate 108 respectively of the left bite tray assembly 104.

The moldable bite insert 1601, is for example, a dental putty, and a dental impression material, used for obtaining imprints of the user's teeth, gums or other structures inside of the user's mouth. The moldable bite inserts 1601 are used in both the top enclosure 106*a* and the bottom enclosure 107*a* for a snug fit of the top bite plate 106 around the portion of the upper teeth and the bottom bite plate 107 around the portion of the lower teeth of the user of the MAD 100. After the fit connector 101 is used to align the left and the right bite tray assemblies 104 and 105 in the mouth of the user, the MAD 100 is heated in boiling water and then placed back in the mouth of the user using the fit connector 101. When bitten into by the user, the moldable bite inserts 1601 conform to the teeth of the user that are covered by the top and bottom bite plates 106 and 107. Hence, the fit connector 101 is used for fitting the MAD 100 to the mouth of the user only for the first time for procuring a dental impression simultaneously in each of the moldable bite inserts 1601 in the top bite plates 106 and the bottom bite plates 107 in the left and the right bite tray assemblies 104 and 105 without allowing movement of the MAD 100. The fit connector 101 is then detached from the left and the right bite tray assemblies 104 and 105. The left and the right bite tray assemblies 104 and 105 are then used independently without the fit connector 101 by the user.

The top connector section 106*b* and the bottom connector section 107*b* are configured as walls on either of the longer sides of the top bite plate 106 and the bottom bite plate 107 respectively. The top connector section 106*b* and the bottom connector section 107*b* that are configured as walls incorporate apertures 111 for detachably attaching the top bite plate 106 and the bottom bite plate 107 respectively to one of the pair of H connectors 102 and for attaching a moldable bite insert 1601 each in the top enclosure 106*a* of the top bite plate 106 and the bottom enclosure 107*a* of the bottom bite plate 107. Of the apertures 111, the frontmost apertures 111*a*, farthest from the hinge pin receptacle 110 are used to attach the left and the right bite tray assemblies 104 and 105 to the H connectors 102. Each of the pair of H connectors 102 has a prong 102*d* at each of the four terminal points of the vertical strokes of the capital letter H, as shown in FIG. 7A. These prongs 102*d* are inserted into the frontmost apertures 111*a* of the top connector section 106*b* and the bottom connector section 107*b* ensuring a detachable attachment. The moldable bite inserts 1601 have protrusions that fit into the remainder of the apertures 111 so that the moldable bite inserts 1601 do not move within the top enclosure 106*a* and the bottom enclosure 107*a* and when fitted in the mouth of the user using the fit connector 101, resulting in a stable fit of the MAD 100 around the teeth of the user.

Figure 3A:
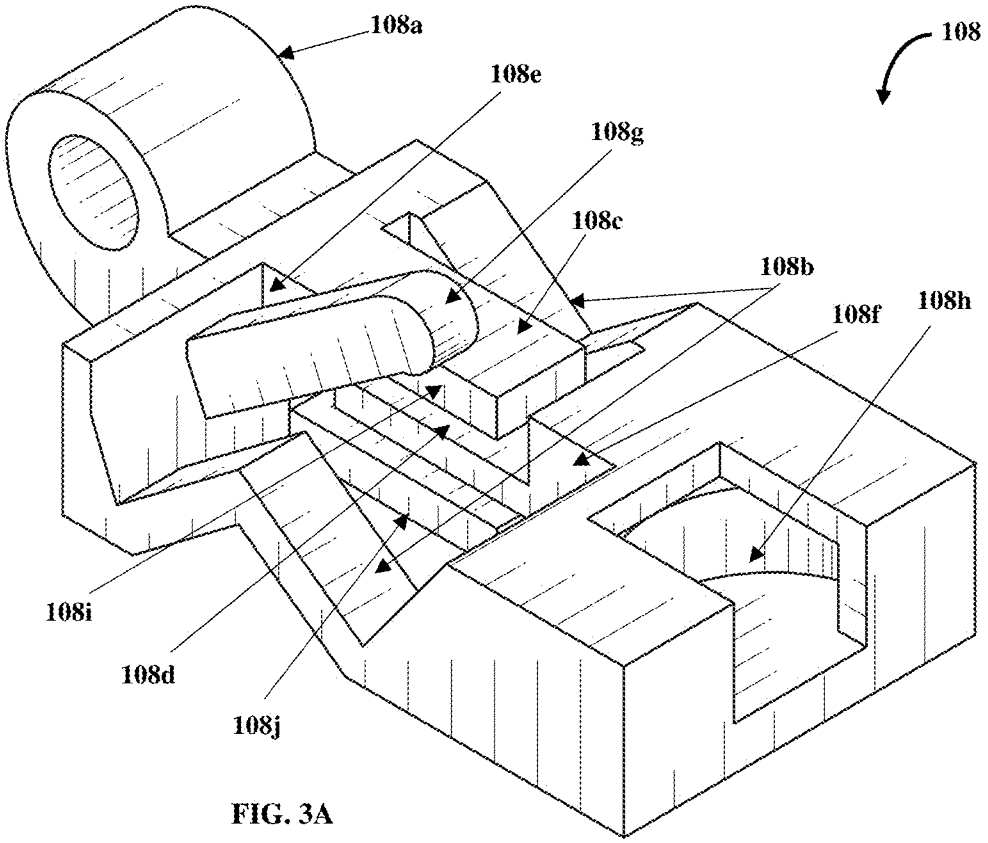
FIGS. 3A-3B illustrate perspective views of a hinge plate of the mandibular advancement device.

The hinge plate 108 is interposed between the top bite plate 106 and the bottom bite plate 107. The hinge plate 108 facilitates protrusion and retraction of the mandible while maintaining a minimum advancement of the mandible when the MAD 100 is in use. The hinge plate 108 comprises an anchor hinge receptacle 108*h*, as shown in FIG. 3A. The hinge plate 108 is operably connected to the bottom bite plate 107 using a circumduction anchor rod 601, which interfaces with the hinge plate 108 via the anchor hinge receptacle 108*h* and with the bottom bite plate 107 via an anchor bottom receptacle 107*c* in the bottom bite plate 107. The operable connection facilitates lateral translation and rotation of the mandible when the MAD 100 is in use. Moreover, the hinge plate 108 comprises the second part 108*a* of the two parts of the hinge pin receptacle 110. The hinge plate 108 is attached to the top bite plate 106 using the pin 109.

Figure 9A:
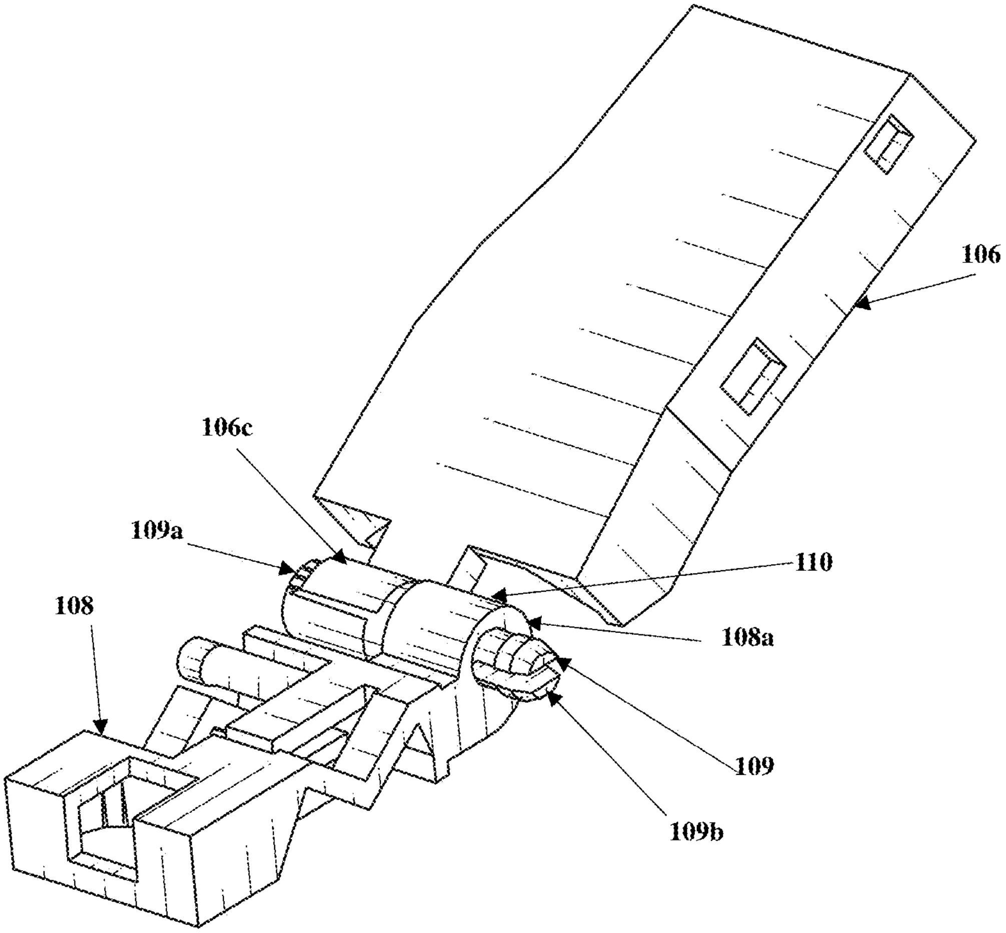
FIGS. 9A-9C illustrate the articulation between the top bite plate and the hinge plate around the pin.

The pin 109 is inserted through the first part 106*c* of the two parts of the hinge pin receptacle 110 in the top bite plate 106 and the second part 108*a* of the two parts of the hinge pin receptacle 110 in the hinge plate 108 and secures the two components in a detachable manner, as illustrated in FIG. 9A. The pin 109 allows relative rotation between the top bite plate 106 and the hinge plate 108, providing an operable connection that facilitates opening and closing of the mandible when the MAD 100 is in use.

Figure 2A:
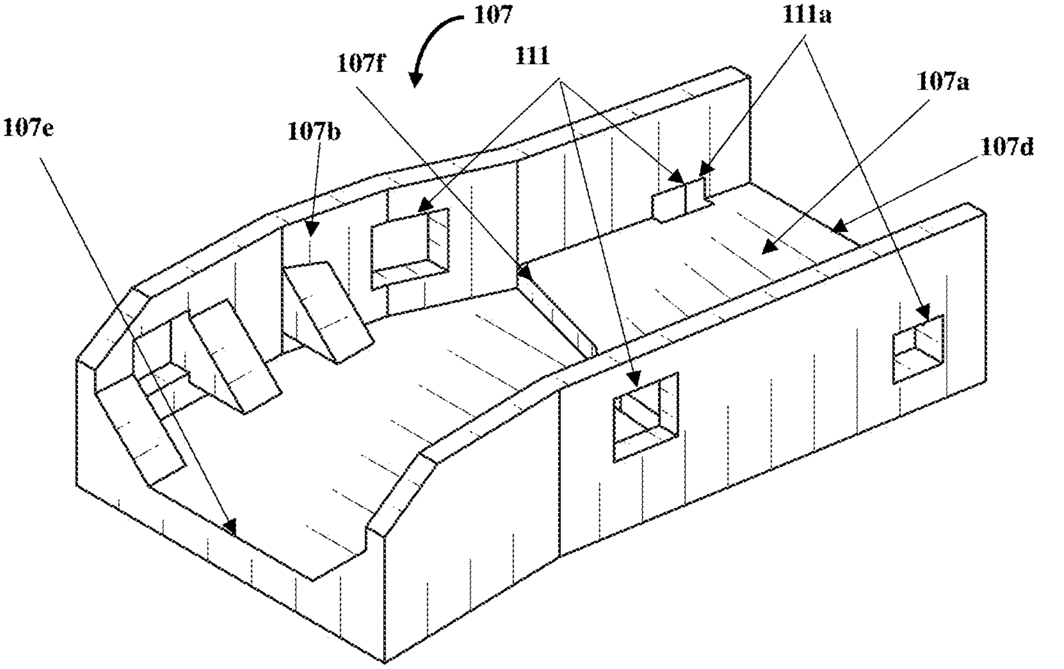
FIGS. 2A-2B illustrate perspective views of a bottom bite plate of the mandibular advancement device.
Figure 2B:
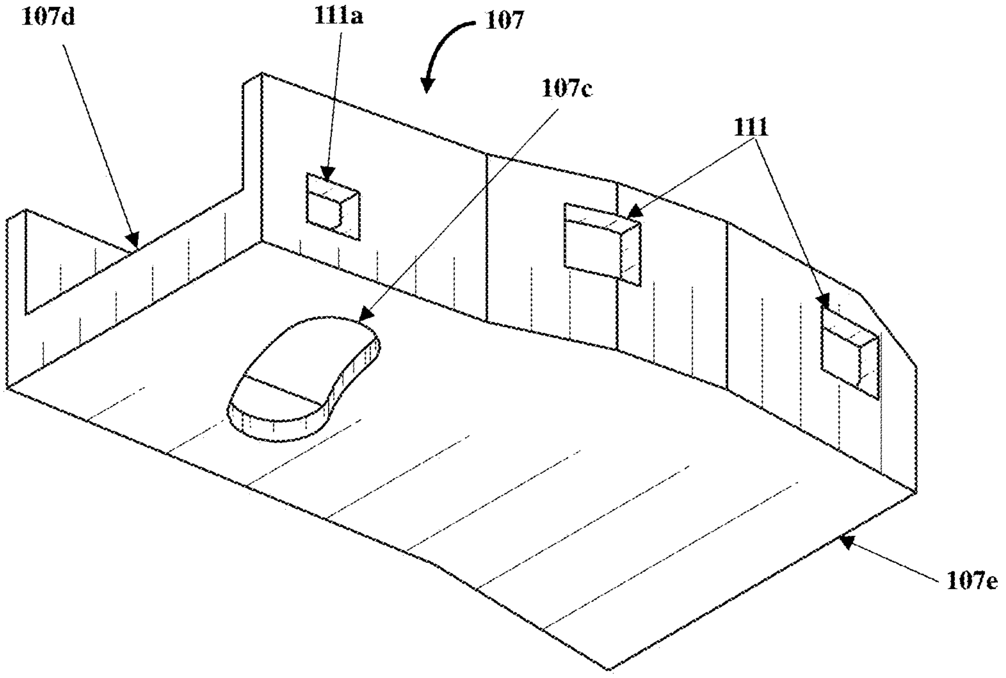

FIGS. 2A-2B illustrate perspective views of a bottom bite plate 107 of the mandibular advancement device 100. As disclosed in the detailed description of FIG. 1, the bottom bite plate 107 comprises the bottom enclosure 107*a*, the bottom connector section 107*b* configured as walls along the length of the bottom bite plate 107 with some of the apertures 111, and an anchor bottom receptacle 107*c*. The bottom bite plate 107 is shaped to accommodate a portion of the lower teeth of a user of the mandibular advancement device (MAD) 100. To that end, the bottom bite plate 107 increases in width from the front at the bottom bite plate front section 107*d* to the back at the bottom bite plate back section 107*e*. Moreover, the bottom enclosure 107*a* has a bottom enclosure shoulder 107*f* that separates the bottom bite plate front section 107*d* and the bottom bite plate back section 107*e* by a change in thickness, with the bottom bite plate front section 107*d* being thicker.

The frontmost apertures 111*a*, near the bottom bite plate front section 107*d*, are smaller than the remainder of the apertures 111 and are designed to accommodate the lower two prongs of one of the pair of H connectors 102 disclosed in the detailed description of FIG. 1. The remainder of the apertures 111 are designed to accommodate protrusions in a moldable bite insert 1601 housed by the bottom enclosure 107*a* to keep the moldable bite insert in place 1601.

The anchor bottom receptacle 107*c* is a hole designed in the shape of an elliptical cylinder in the bottom enclosure 107*a* at the bottom bite plate front section 107*d* for receiving one end of a circumduction anchor rod 601 that connects the bottom bite plate 107 to the hinge plate 108 as disclosed in the detailed description of FIG. 1. The anchor bottom receptacle 107*c* is shaped as an elliptical cylinder to securely hold the end of the circumduction anchor rod 601 in place, preventing it from disengaging during use, and to permit articulation in the form of lateral translation and rotation between the bottom bite plate 107 and the circumduction anchor rod 601, with the end of the circumduction anchor rod 601 positioned within the anchor bottom receptacle 107*c*. To remove the end of the circumduction anchor rod 601 from the anchor bottom receptacle 107*c*, the bottom bite plate 107 is rotated by a ninety-degree-angle and withdrawn at an angle.

Figure 3B:
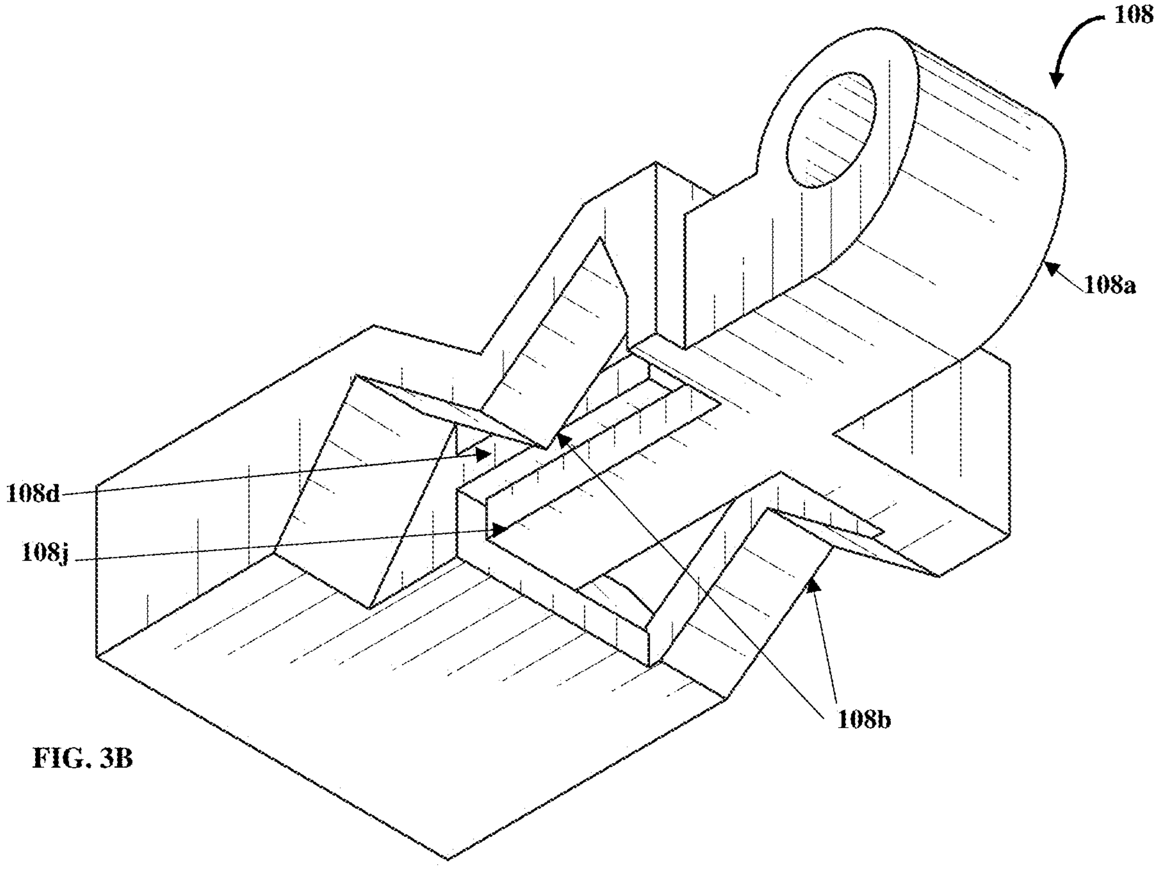
Figure 10A:
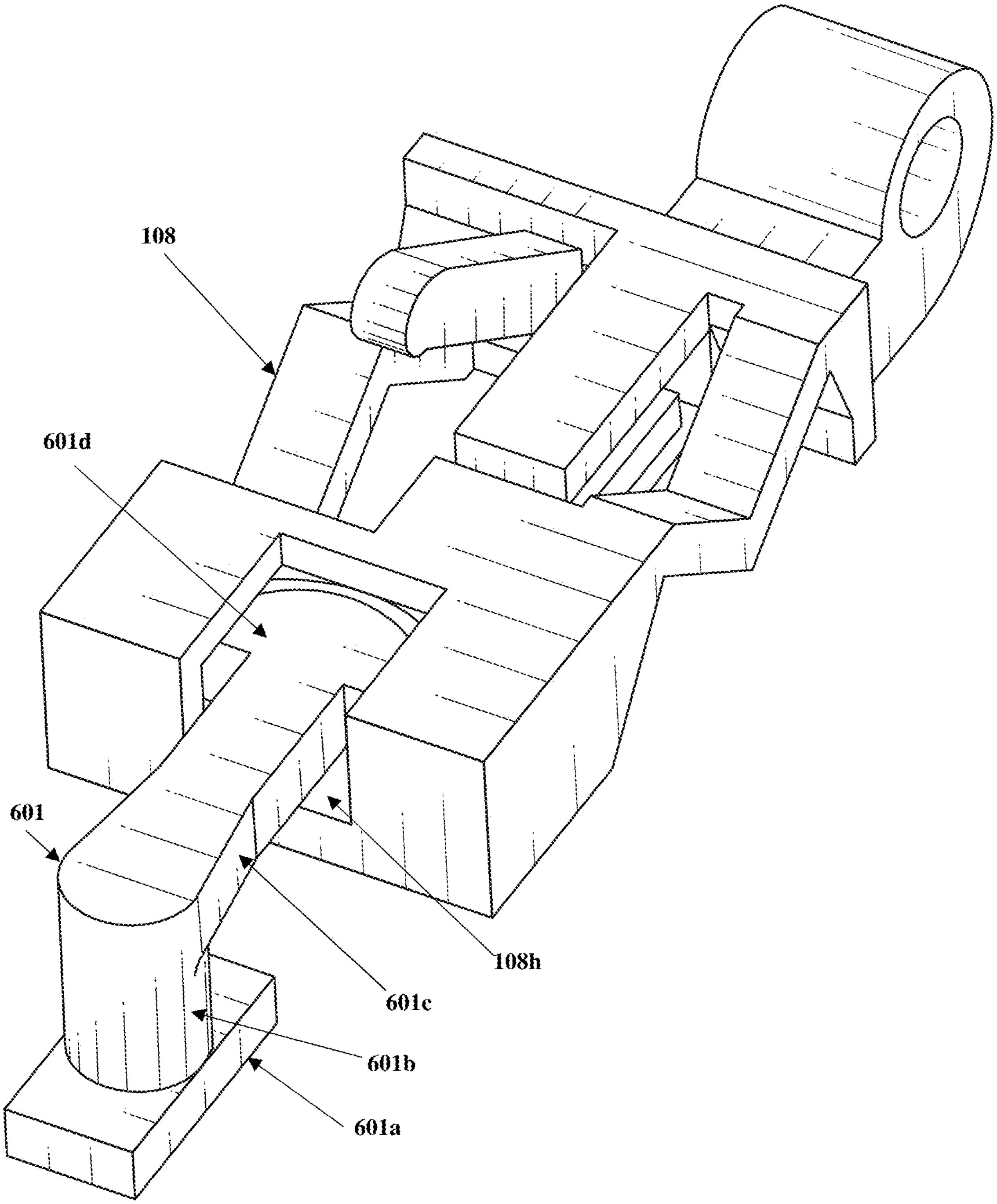
FIGS. 10A-10C illustrate the articulation between the hinge plate and the circumduction anchor rod.

FIGS. 3A-3B illustrate perspective views of a hinge plate 108 of the mandibular advancement device 100. As disclosed in the detailed description of FIG. 1, the hinge plate 108 comprises the second part 108*a* of the two parts of the hinge pin receptacle 110. The hinge plate 108 comprises a flexible member 108*b*, a dentate member 108*c*, a tension prong 108*g*, and an anchor hinge receptacle 108*h*. The second part 108*a* of the two parts of the hinge pin receptacle 110 receives a pin 109 shown in FIGS. 5A and 5B, that operably connects the hinge plate 108 to the top bite plate 106, as shown in FIG. 9A, facilitating opening and closing of the mandible when the mandibular advancement device (MAD) 100 is in use in the user's mouth as disclosed in the detailed description of FIG. 1. The anchor hinge receptacle 108*h* receives one end of a circumduction anchor rod 601 that connects the hinge plate 108 to the bottom bite plate 107 as disclosed in the detailed description of FIG. 1. The anchor hinge receptacle 108*h* is a depression in the hinge plate 108 designed in a semi-cylindrical shape with the entry to the anchor hinge receptacle 108*h* being smaller than the anchor hinge receptacle 108*h* itself, as shown in FIG. 10A, requiring the end of the circumduction anchor rod 601 to be inserted at an angle through the entry. Once inserted, the circumduction anchor rod 601 remains securely attached during normal use of the MAD 100 while the semi-cylindrical shape of the anchor hinge receptacle 108*h* permits lateral translation between the hinge plate 108 and the bottom bite plate 107 when the circumduction anchor rod 601 is also connected to the bottom bite plate 107, with the one end of the circumduction anchor rod 601 positioned within the anchor hinge receptacle 108*h* and the other positioned within the anchor bottom receptacle 107*c* of the bottom bite plate 107.

The tension prong 108*g* provides tension when a user of the mandibular advancement device (MAD) 100 opens and closes the mouth for providing a stable fit of the MAD 100 in the mouth. When the MAD 100 is in use, the flexible member 108*b*, comprising a component each on either side of the length of the hinge plate 108, extends and contracts for protrusion and retraction of the hinge plate 108 when the mouth is opened and closed respectively by the user of the MAD 100.

The maximum contraction of the flexible member 108*b* is dictated by the dentate member 108*c*. The dentate member 108*c* is positioned at the center of the hinge plate 108 between the two components of the flexible member 108*b* and has three rectangular segments 108*d*, 108*i* and 108*j* with their lengths aligned along the length of the hinge plate 108. Two of the rectangular segments 108*i* and 108*j* are attached to a first end 108*e* of the dentate member 108*c* that is along the width of the hinge plate 108 with a defined gap between them. The third rectangular segment 108*d* is attached to a second end 108*f* of the dentate member 108*c* opposing the first end 108*e* and is positioned vertically within the gap between the other two rectangular segments 108*i* and 108*j*.

When the flexible member 108*b* contracts, bringing the two opposing ends of the dentate member 108*c* closer together, the distance to which they can approach one another is limited by the lengths of the rectangular segments 108*d*, 108*i* and 108*j*. As the first end 108*e* and the second end 108*f* of the dentate member 108*c* converge, the third rectangular segment 108*d* comes into contact with the first end 108*e*, making contact within the gap between the first two rectangular segments 108*i* and 108*j* while the first two rectangular segments 108*i* and 108*j* make contact with the second end 108*f*. Therefore, the dentate member 108*c* limits the retraction of the hinge plate 108 when the MAD 100 is in use and maintains a minimum advancement of the mandible.

Figure 4A:
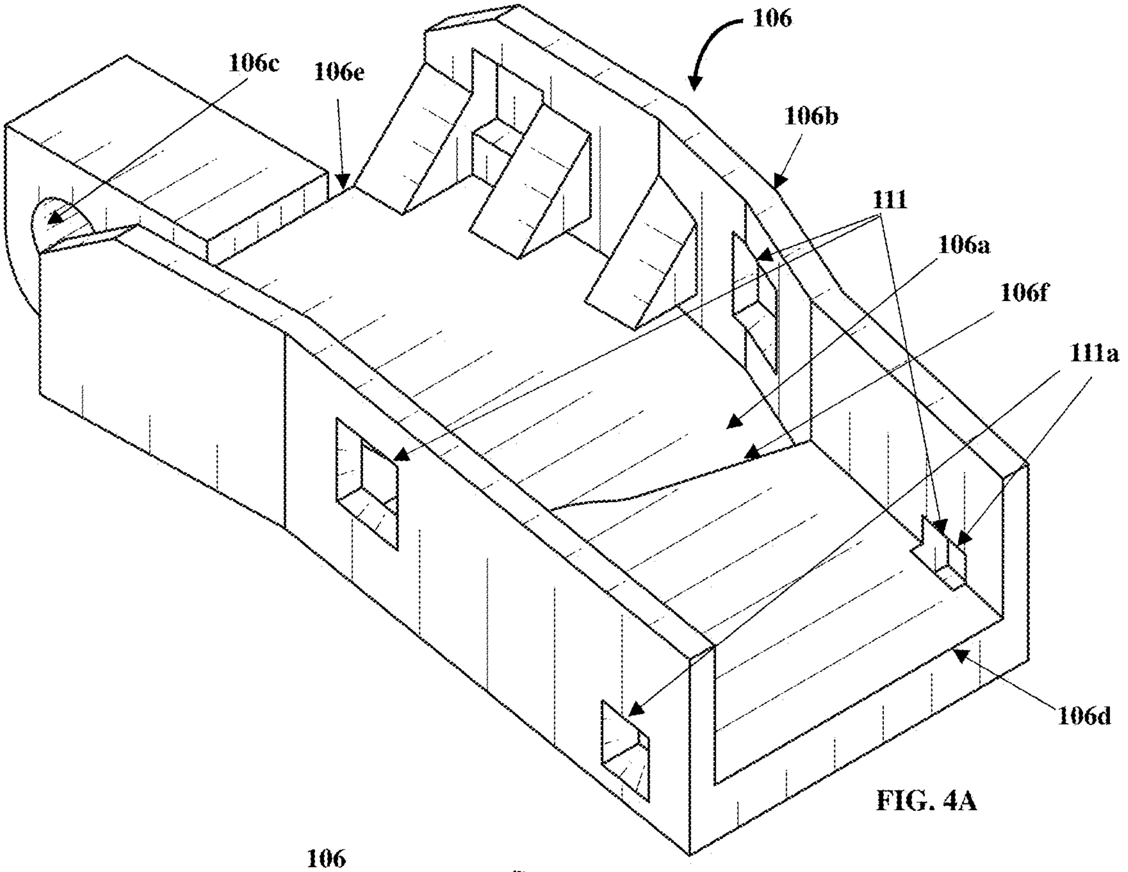
FIGS. 4A-4B illustrate perspective views of a top bite plate of the mandibular advancement device.
Figure 4B:
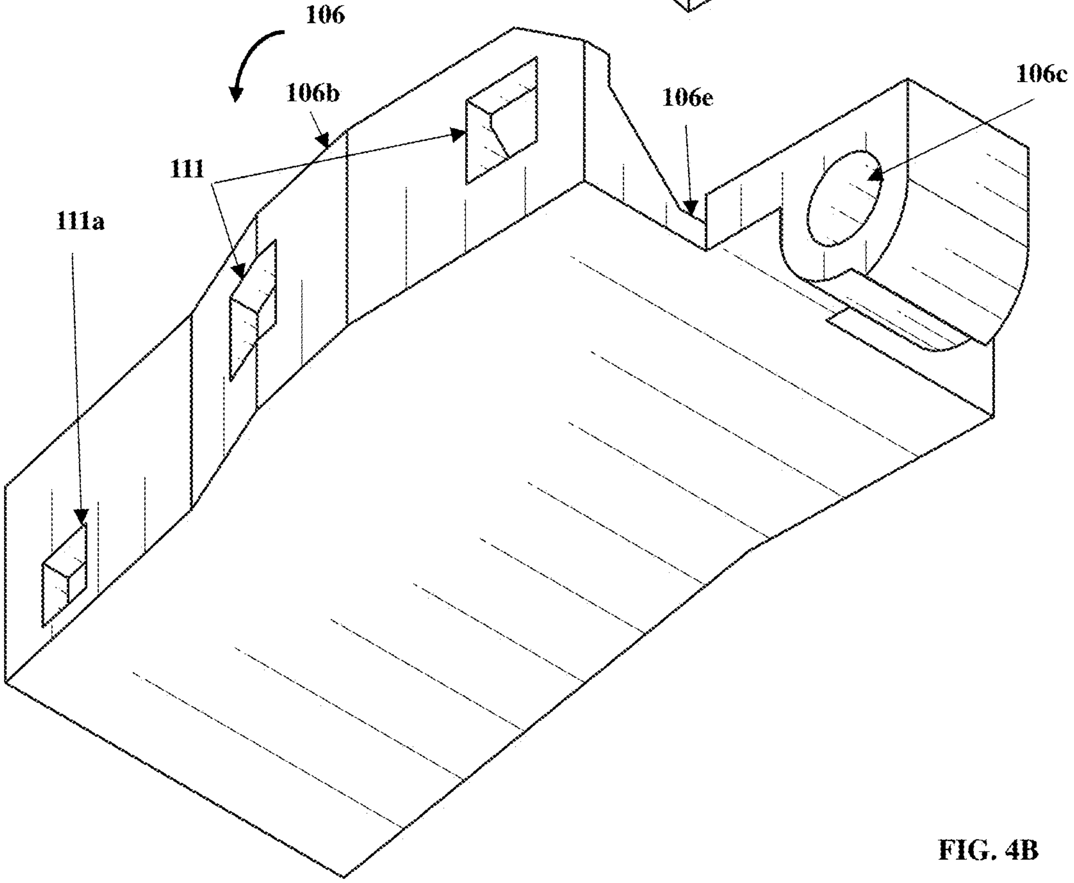

FIGS. 4A-4B illustrate perspective views of a top bite plate 106 of the mandibular advancement device 100. As disclosed in the detailed description of FIG. 1, the top bite plate 106 comprises the top enclosure 106*a*, the top connector section 106*b* configured as walls along the length of the top bite plate 106 with some of the apertures 111, and the first part 106*c* of the two parts of the hinge pin receptacle 110. The top bite plate 106 is shaped to accommodate a portion of the upper teeth of the user of the mandibular advancement device (MAD) 100. To that end, the top bite plate 106 increases in width from the front at the top bite plate front section 106*d* to the back at the top bite plate back section 106*e*. The top enclosure 106*a* has a top enclosure shoulder 106*f* that separates the top bite plate front section 106*d* and the top bite plate back section 106*e* by a change in thickness, the top bite plate front section 106*d* being thicker.

The frontmost apertures 111*a*, farthest from the first part 106*c* of the two parts of the hinge pin receptacle 110, are smaller than the remainder of the apertures 111 and are designed to accommodate the upper two prongs 102*d* of one of the pair of H connectors 102 disclosed in the detailed description of FIG. 1. The remainder of the apertures 111 are designed to accommodate protrusions in a moldable bite insert 1601 housed by the top enclosure 106*a* to keep the moldable bite insert 1601 in place.

Figure 5A:
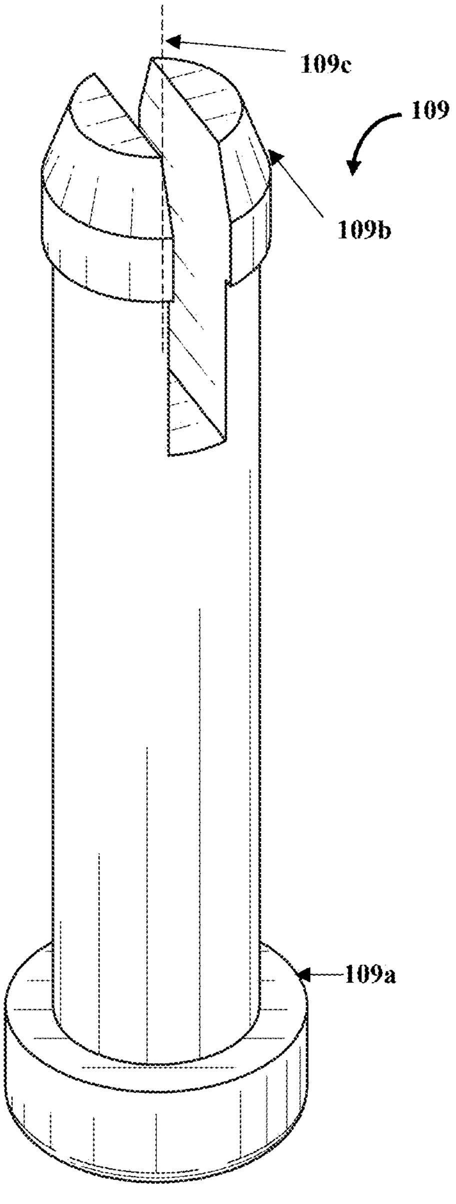
FIGS. 5A-5B illustrate perspective views of a pin of the mandibular advancement device.
Figure 5B:
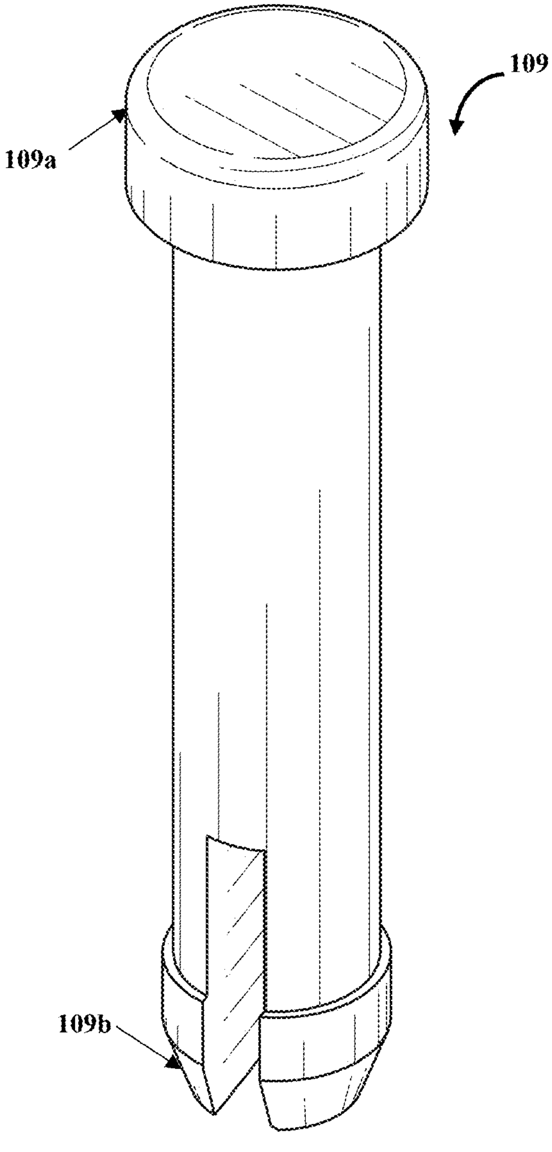

When the mandibular advancement device (MAD) 100 is assembled, the first part 106*c* of the two parts of the hinge pin receptacle 110 is positioned in alignment with the second part 108*a* of the two parts of the hinge pin receptacle 110, where the hinge pin receptacle 110 and the second part 108*a* are components of the hinge plate 108, as disclosed in the detailed description of FIGS. 4 and 5. A pin 109, shown in FIGS. 5A and 5B, is inserted through both the parts of the hinge pin receptacle 110, as shown in FIG. 9A, configured to prevent disengagement during normal use of the MAD 100, thereby securely connecting the top bite plate 106 to the hinge plate 108. The connection is also operable allowing relative rotation of the top bite plate 106 and the hinge plate 108.

FIGS. 5A-5B illustrate perspective views of a pin 109 of the mandibular advancement device. As disclosed in the detailed descriptions of FIG. 1 and FIGS. 4A-4B, the pin 109 connects the hinge plate 108 to the top bite plate 106 while permitting relative rotation between the hinge plate 108 and the top bite plate 106 to facilitate opening and closing of the mandible when the mandibular advancement device (MAD) 100 is in use. The pin is inserted through the first part 106*c* of the two parts of the hinge pin receptacle 110 in the top bite plate 106 and the second part 108*a* of the two parts of the hinge pin receptacle 110 in the hinge plate 108, detachably securing the top bite plate 106 and the hinge plate 108.

One end of the pin 109 has a head 109*a* that is larger than the diameter of the hinge pin receptacle 110 through which the pin 109 passes. The opposite end of the pin 109 is designed as a split end 109*b* that flexes towards a central axis 109*c* of the pin 109 when pushed through the hinge pin receptacle 110 from one side, but does not return to its original position when pulled once the pin 109 is in place in the hinge pin receptacle 110. To remove the pin 109, the two portions of the split end 109*b* must be manually pressed toward each other, towards the central axis 109*c*, allowing the pin 109 to be withdrawn from the hinge pin receptacle 110. Consequently, the pin 109 provides a secure connection between the top bite plate 106 and the hinge plate 108 while also permitting relative rotation between them, facilitating articulation about the pin 109 when the top bite plate 106 and the hinge plate 108 are attached.

Figure 6A:
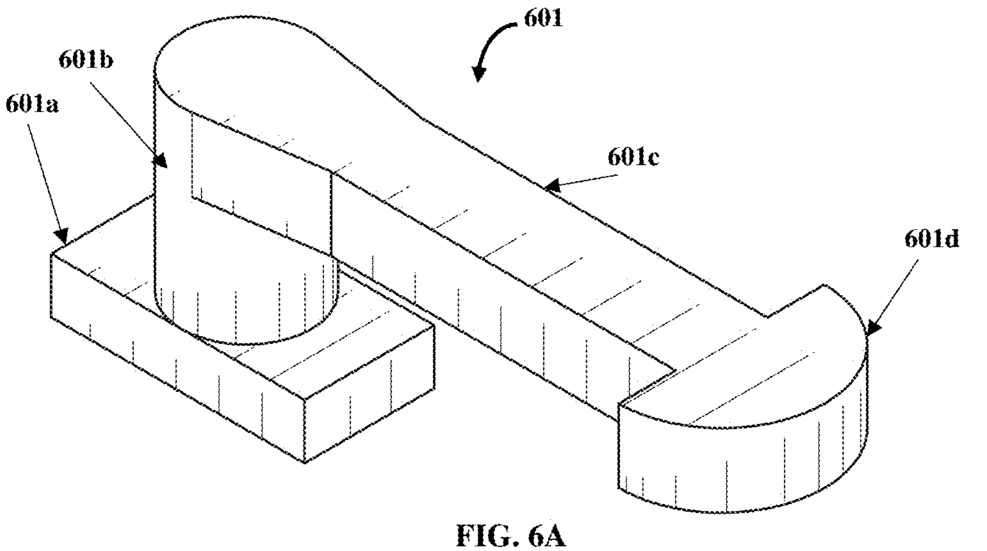
FIGS. 6A-6H illustrate perspective views of different embodiments of a circumduction anchor rod of the mandibular advancement device.
Figure 6B:
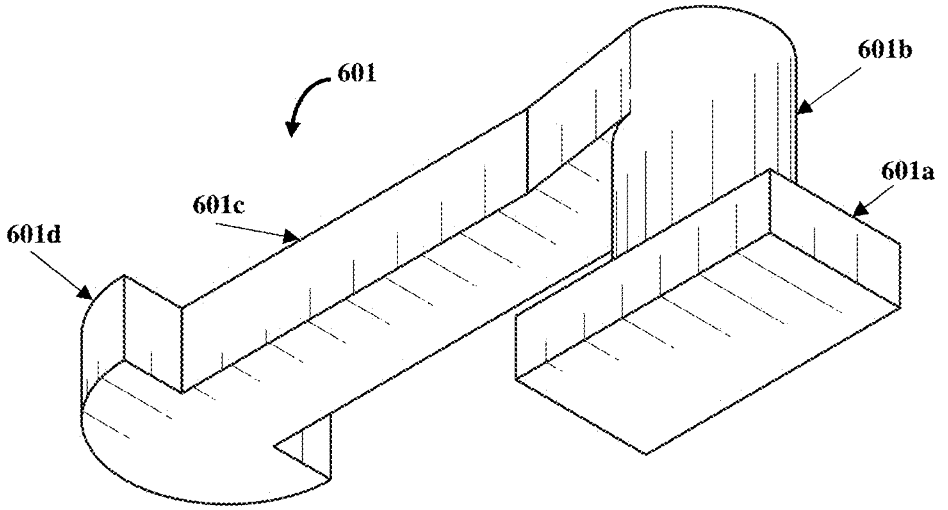
Figure 6C:
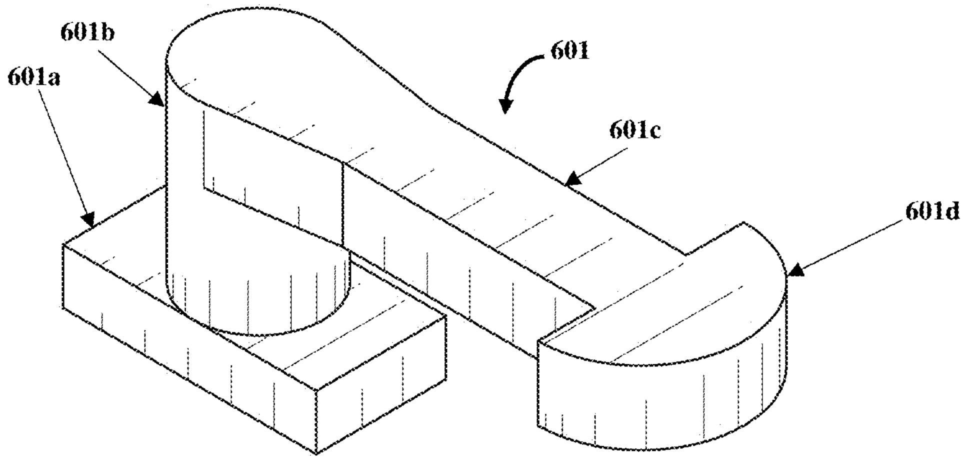
Figure 6D:
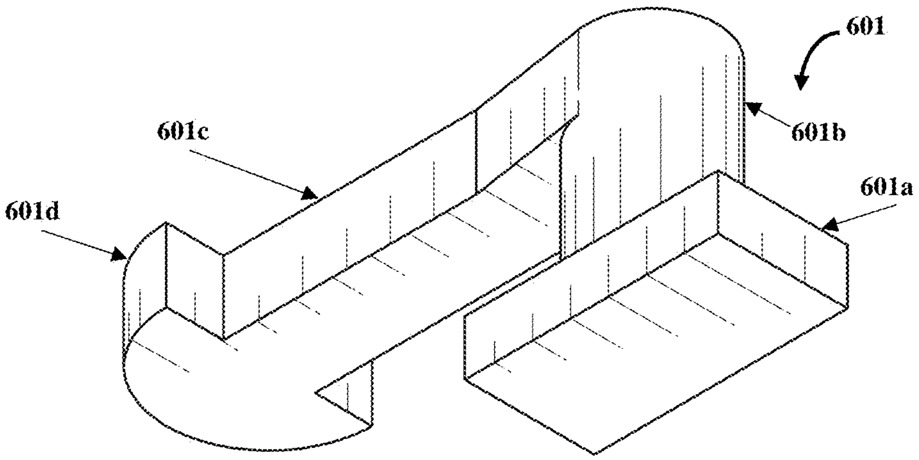
Figure 6E:
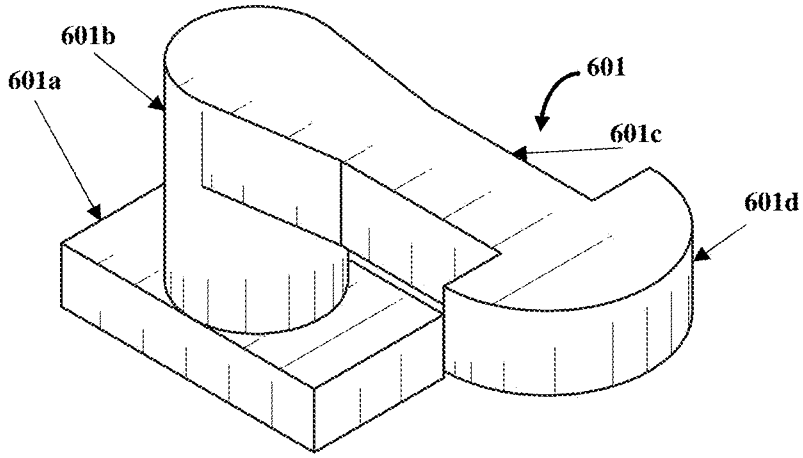
Figure 6F:
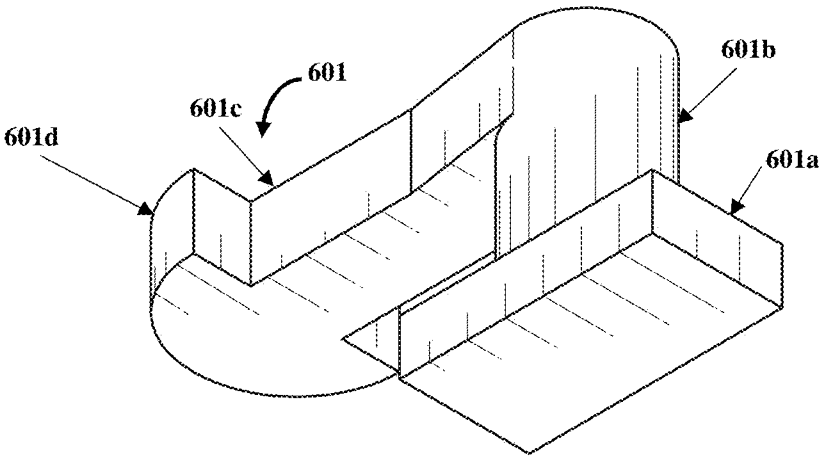
Figure 6G:
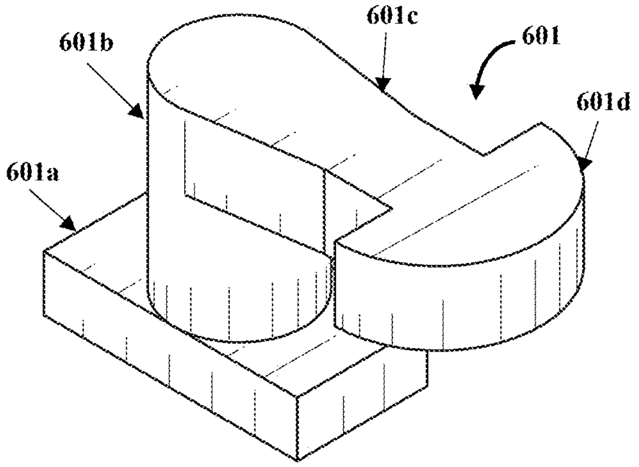
Figure 6H:
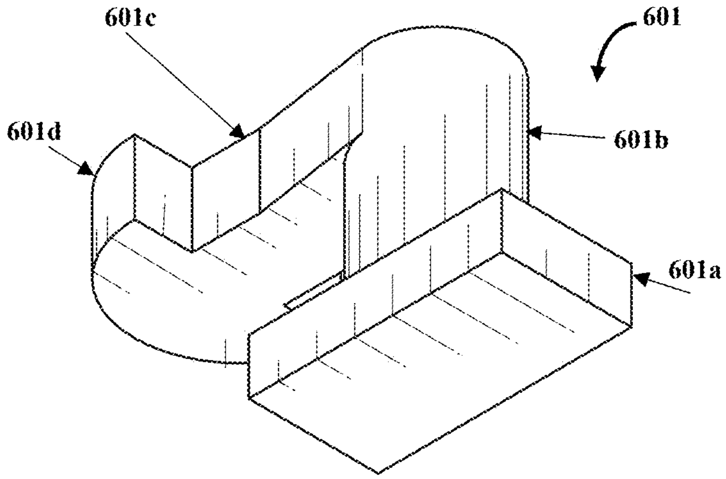

FIGS. 6A-6H illustrate perspective views of different embodiments of a circumduction anchor rod 601 of the mandibular advancement device 100. The circumduction anchor rod 601 comprises an anchor rod bottom section 601*a*, an anchor rod post 601*b*, an anchor rod middle section 601*c*, and an anchor rod front section 601*d*. The anchor rod post 601*b* is a cylinder of a predetermined diameter and height and is connected to the anchor rod front section 601*d* by the anchor rod middle section 601*c*. The anchor rod middle section 601*c* extends perpendicularly from a top of the anchor rod post 601*b* while a bottom of the anchor rod post 601*b* is attached to the anchor rod bottom section 601*a*. The different embodiments of the circumduction anchor rod 601 differ only in the length of the anchor rod middle section 601*c* with FIGS. 6C and 6D illustrating the neutral embodiment of the circumduction anchor rod 601. The neutral embodiment of the circumduction anchor rod 601 is used in both the left and the right bite tray assemblies 104 and 105 when the mandibular advancement device (MAD) 100 is being fitted to the mouth of a user for the first time using the fit connector 101 as disclosed in the detailed description of FIG. 1. Subsequently, the fit connector 101 is removed from the left and the right bite tray assemblies 104 and 105 and, based on a required level of mandibular advancement 100, a corresponding embodiment of the circumduction anchor rod 601 of suitable length is inserted, one each in the left bite tray assembly 104 and the right bite tray assembly 105.

The anchor rod bottom section 601*a* is cuboidal in shape and is inserted into the anchor bottom receptacle 107*c* of the bottom bite plate 107 to achieve a secure and operable connection between the circumduction anchor rod 601 and the bottom bite plate 107 that allows lateral translation and rotation between them as disclosed in the detailed description of FIGS. 2A-2B. The anchor rod front section 601*d* is semi-cylindrical in shape and is inserted into the anchor hinge receptacle 108*h* of the hinge plate 108 to achieve a secure and operable connection between the circumduction anchor rod 601 and the hinge plate 108 that allows lateral translation between the hinge plate 108 and the bottom bite plate 107 as disclosed in the detailed description of FIGS. 3A-3B. Therefore, the circumduction anchor rod 601 operably connects the hinge plate 108 to the bottom bite plate 107 facilitating lateral translation and rotation of the mandible while the mandibular advancement device (MAD) 100 is in use.

Figure 7B:
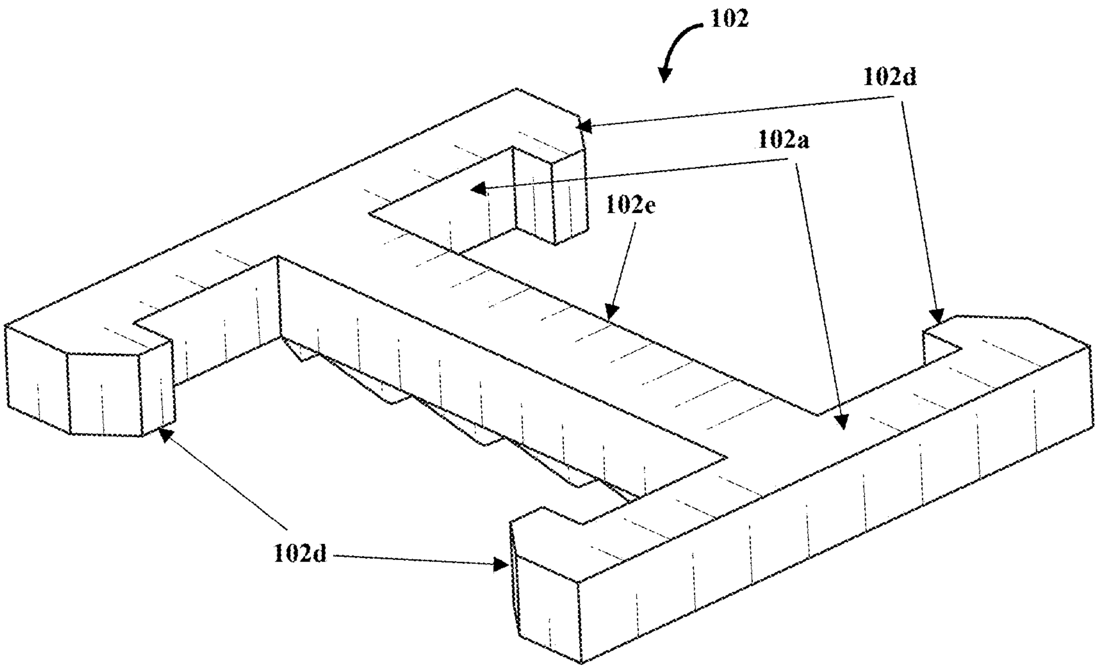
Figure 7C:
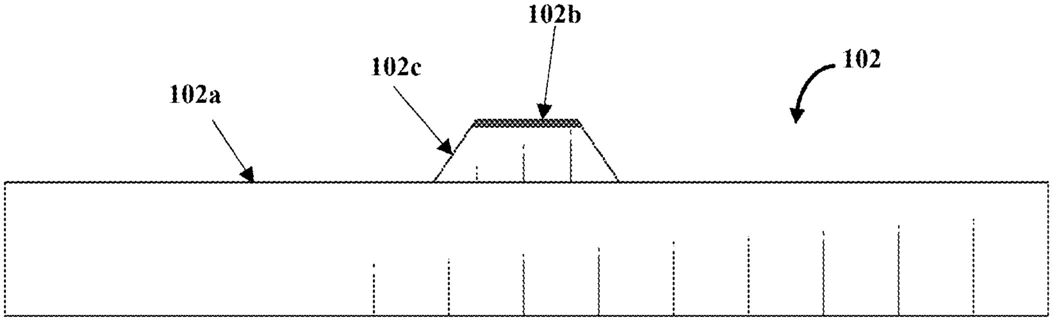
FIG. 7C illustrates a right-side view of the H connector of the mandibular advancement device.

FIGS. 7A-7B illustrate perspective views of a H connector of the mandibular advancement device. FIG. 7C illustrates a right-side view of the H connector of the mandibular advancement device. As disclosed in the detailed description of FIG. 1, the H connectors 102 are parts of the fit connector 101 and are in the shape of the capital letter H. Each of the H connectors 102 comprises two vertical strokes 102*a*, a crossbar 102*e* with a zigzag track 102*b* with its lateral sides

102*c*, and prongs 102*d*, one each at each of the four terminal points of the vertical strokes 102*a*. The prongs are inserted into the frontmost apertures 111*a* of the top connector section 106*b* of the top bite plate 106 and the bottom connector section 107*b* of the bottom bite plate 107 to provide a secure but detachable attachment between the H connectors 102 and the left and the right bite tray assemblies 104 and 105 as disclosed in the detailed descriptions of FIGS. 1, 2A-2B, and 4A-4B. The crossbar 102*e* with its zigzag track 102*b* of each of the H connectors 102 is placed into the guide slot 103*d* in each of the arms of the Y connector 103 to detachably attach the H connectors 102 to the Y connector 103 as disclosed in the detailed description of FIG. 1. The zigzag track 102*b* forms upward and downward undulations along the length of the crossbar 102*e*. The lateral sides 102*c* of the zigzag track 102*b* gradually slope inward towards the center of the width of the crossbar 102*e* so that the crossbar 102*e* can be inserted into the guide slot 103*d* in an arm of the Y connector 103 by easing the sloping lateral sides 102*c* into the guide slot 103*d*.

Figure 8B:
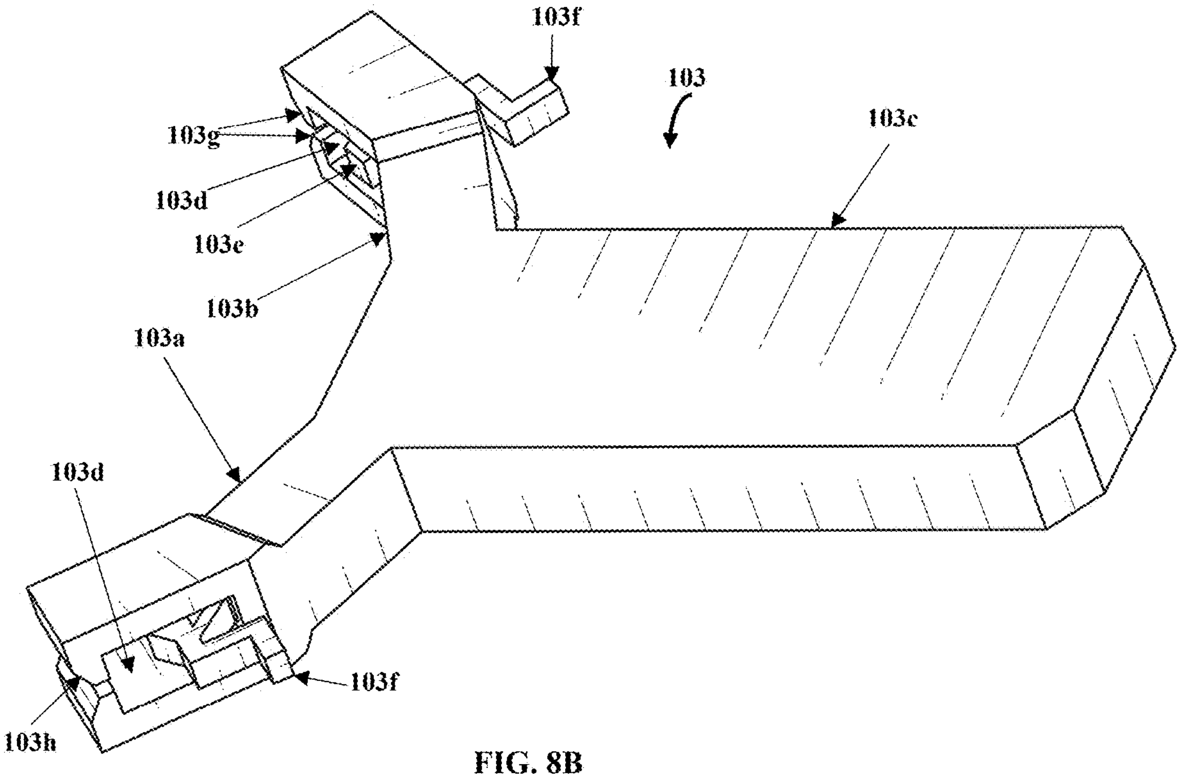
Figure 8C:
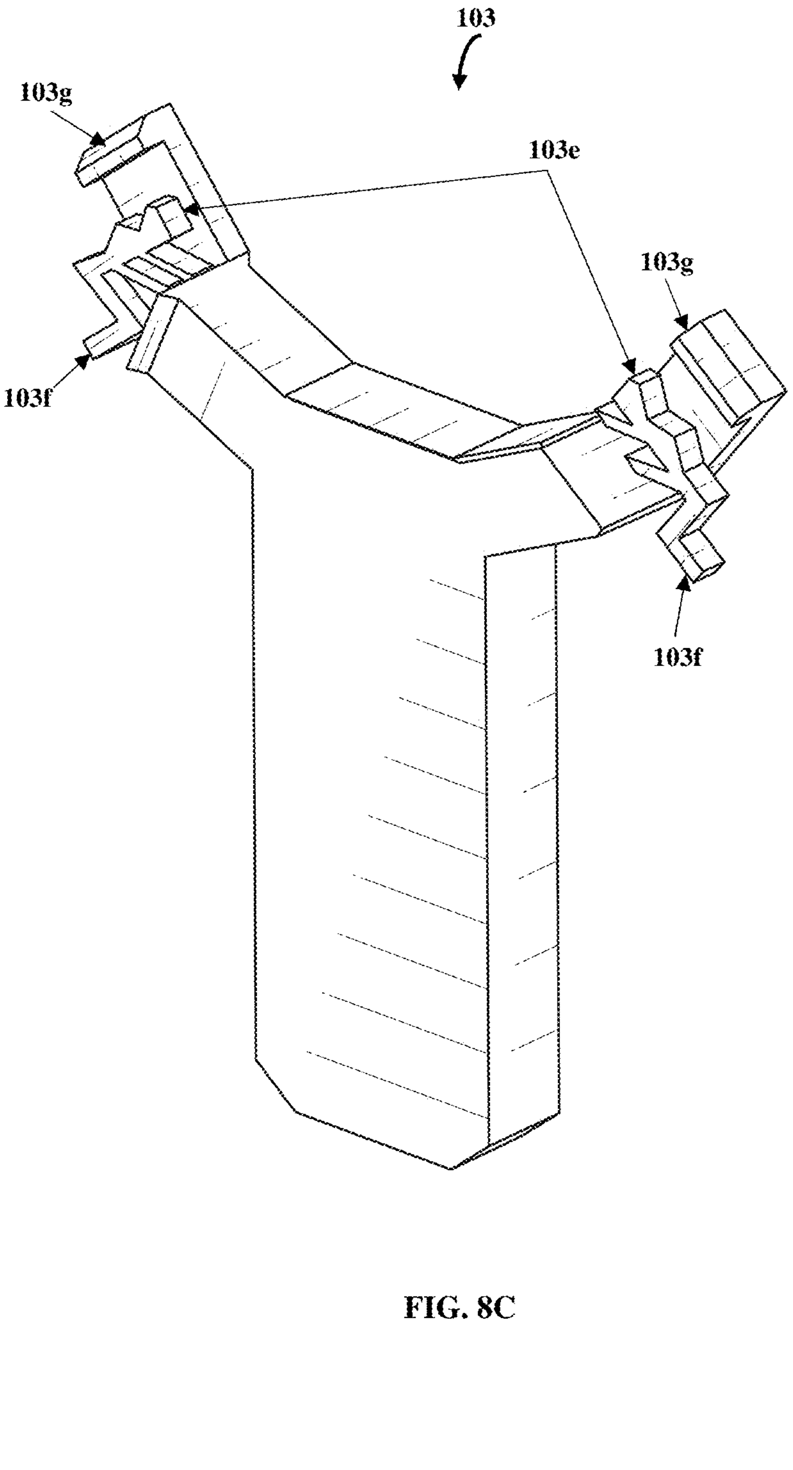

FIGS. 8A-8C illustrate perspective views of a Y connector of the mandibular advancement device. As disclosed in the detailed description of FIG. 1, the Y connector 103 is a part of the fit connector 101 and is in the shape of the capital letter Y. The Y connector 103 comprises two arms 103*a* and 103*b*, a stem 103*c*, a guide slot 103*d* on each of the arms 103*a* and 103*b*, and an engagement pin 103*e* and a lock lever 103*f* in each guide slot 103*d*. The guide slot 103*d* on each of the arms 103*a* and 103*b* receives the crossbar 102*e* with the zigzag track 102*b* of one of the H connectors 102 disclosed in the detailed description of FIGS. 7A-7B. The outermost edges 103*g* of the arms 103*a* and 103*b*, adjacent to the entrance 103*h*, shown in FIGS. 8A and 8B, of the guide slot 103*d* and forming the point of initial contact with the crossbar 102*e* of the H connectors 102 are beveled so that the zigzag track 102*b* can be eased into the guide slot 103*d* via the sloping lateral sides 102*c* of the zigzag track 102*b*. Once the crossbar 102*e* with the zigzag track 102*b* is placed in the guide slot 103*d*, the crossbar 102*e* is securely held by the arm 103*a* or 103*b* without allowing the crossbar 102*e* to fall out of the guide slot 103*d*. To remove the H connector 102 from the Y connector 103, the H connector 102 is pulled out from the guide slot 103*d* manually with a predetermined force.

The engagement pin 103*e* is a zigzag-shaped locking element that can pulled back away from the opening or entrance 103*h* of the guide slot 103*d* using the lock lever 103*f*, which is connected to the engagement pin 103*e*, as illustrated in FIG. 8C. The connection between the guide slot 103*d* and the engagement pin 103*e* and the lock lever 103*f* is flexible allowing the lock lever 103*f* to be pushed back when pressure is applied on the engagement pin 103*e* from the side of the opening of the guide slot 103*d*. When the zigzag track 102*b* on the crossbar 102*e* of one of the H connectors 102 is placed in the guide slot 103*d*, the engagement pin 103*e* engages with one of the positions on the zigzag track 102*b* to hold it in place. When the zigzag track 102*b* is slid along the guide slot 103*d* with application of a force, the engagement pin 103*e* disengages from its initial position, pushing back the lock lever 103*f*, and locks into the next position on the zigzag track 102*b*, falling into a groove of the zigzag track 102*b* and securing the H connector 102 in place. Therefore, the H connectors 102 can be moved side to side along the guide slots 103*d* of the Y connector 103 while providing a secure connection at each position. A person fitting the mandibular advancement device (MAD) 100 in the mouth of a user holds the MAD 100 with the assembled left and right bite tray assemblies 104 and 105 connected to the H connectors 102, which in turn are connected to the Y connector 103, by the stem 103*c* of the Y connector 103.

Figure 9B:
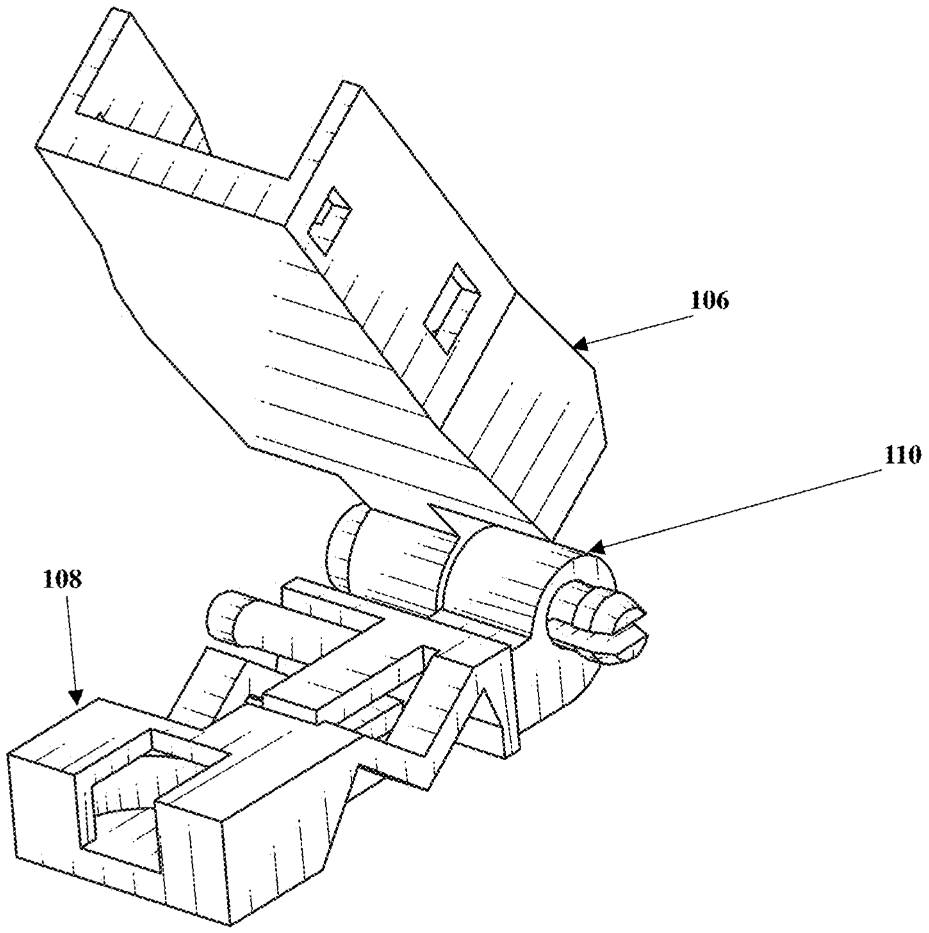
Figure 9C:
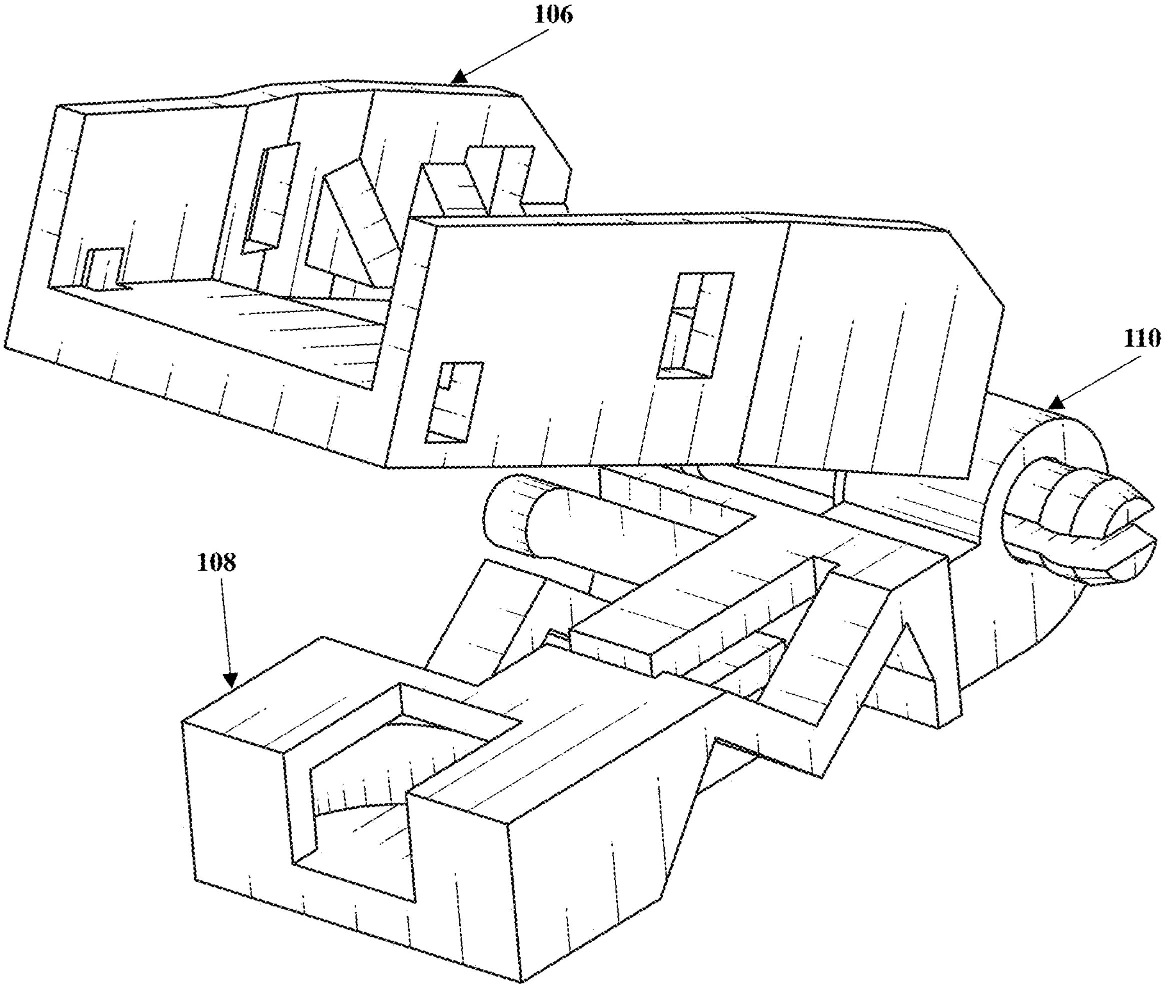

FIGS. 9A-9C illustrate the articulation between the top bite plate 106 and the hinge plate 108 around the pin 109. The pin 109, with its head 109*a* and the split end 109*b* provides a secure yet detachable and operable connection between the top bite plate 106 and the hinge plate 108 as disclosed in the detailed description of FIGS. 5A-5B. The relative rotation between the top bite plate 106 and the hinge plate 108 facilitate opening and closing of the mouth of a user of the mandibular advancement device (MAD) 100.

Figure 10B:
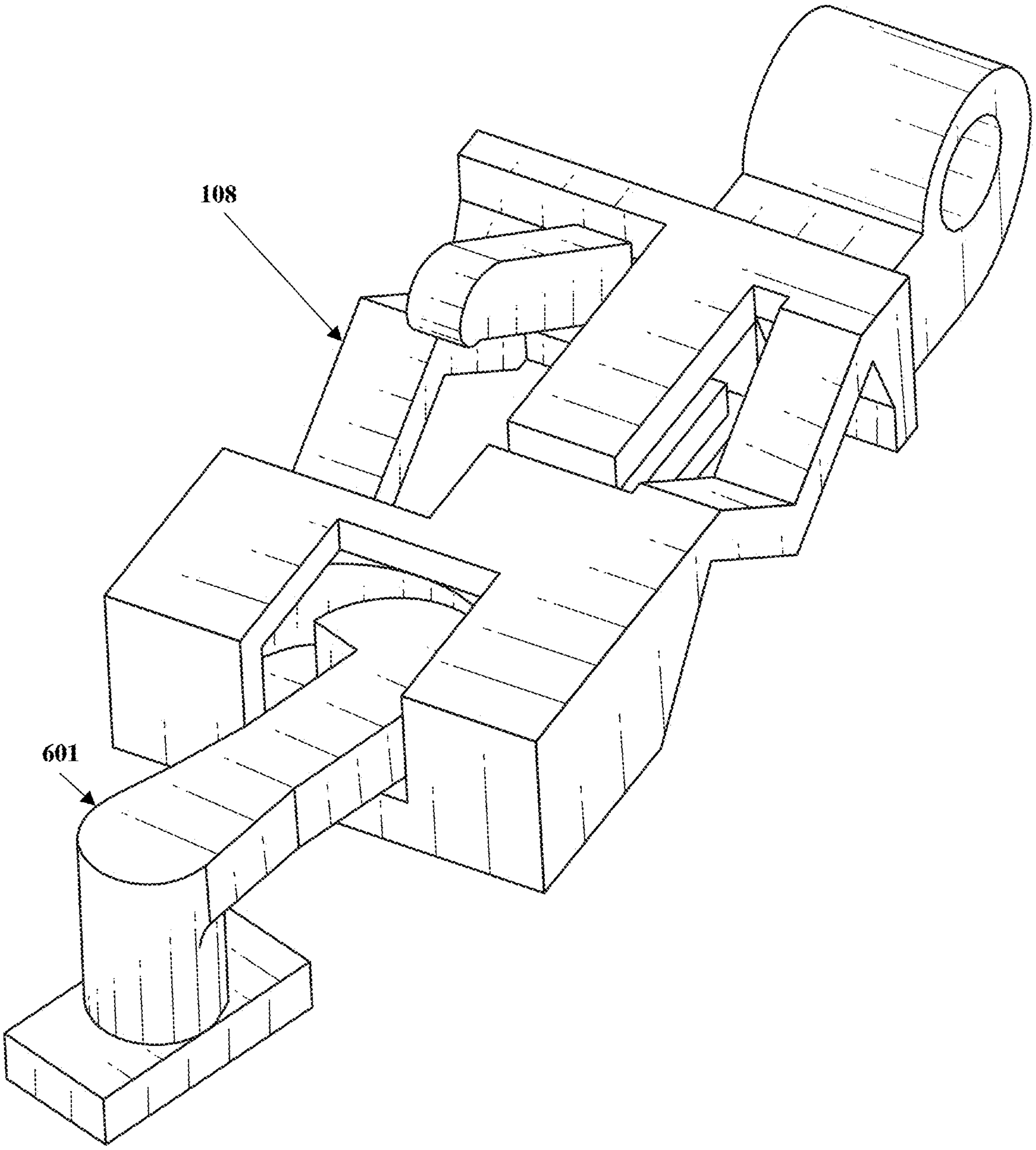
Figure 10C:
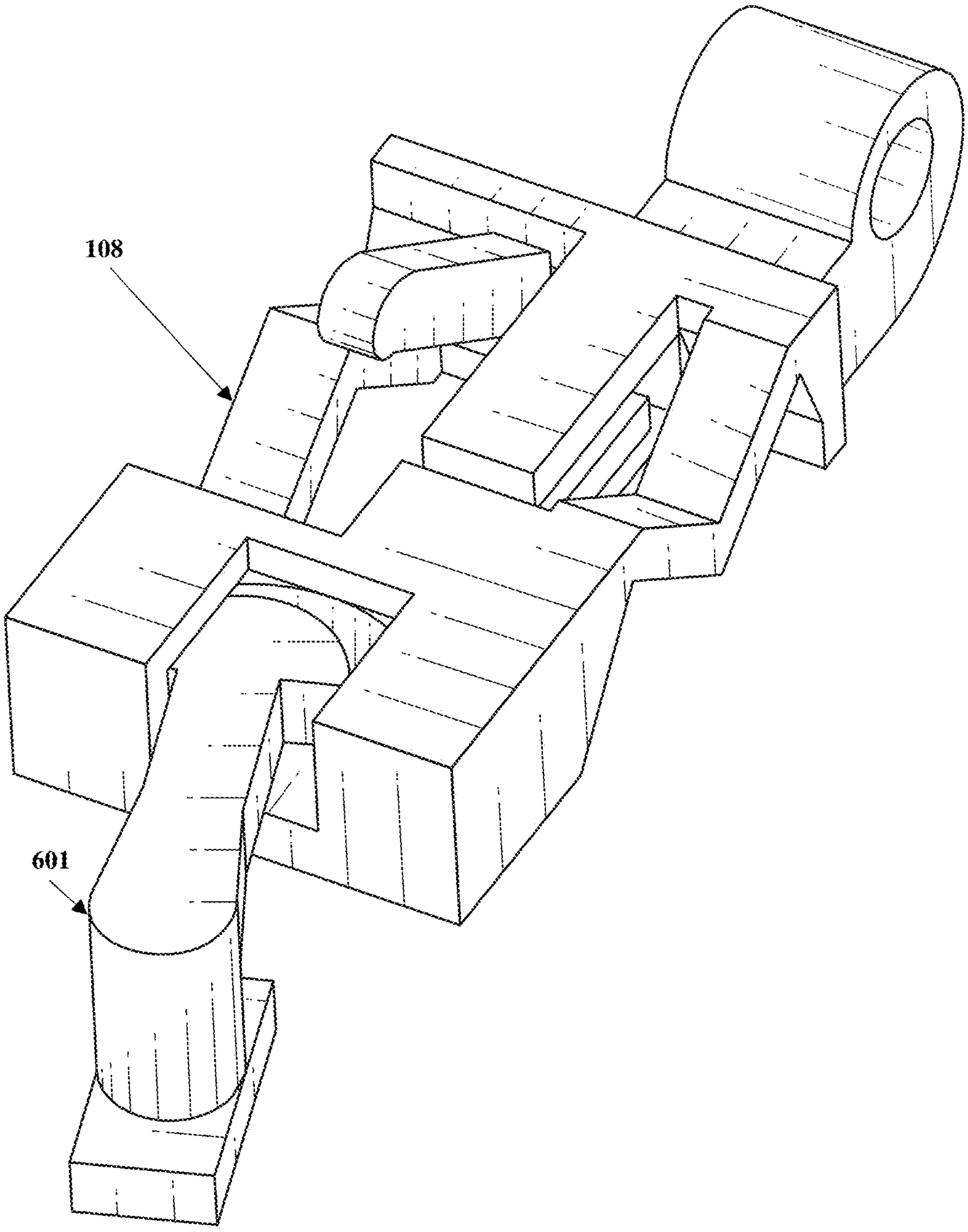

FIGS. 10A-10C illustrate the articulation between the hinge plate 108 and the circumduction anchor rod 601. The anchor rod front section 601*d* of the circumduction anchor rod 601 is inserted into the anchor hinge receptacle 108*h* in the hinge plate 108, providing an operable connection that permits movement of the circumduction anchor rod 601 facilitating lateral translation between the hinge plate 108 and the bottom bite plate 107 when the anchor rod bottom section 601*a* is inserted into the anchor bottom receptacle 107*c* in the bottom bite plate 107 as disclosed in the detailed description of FIGS. 6A-6H.

Figure 11A:
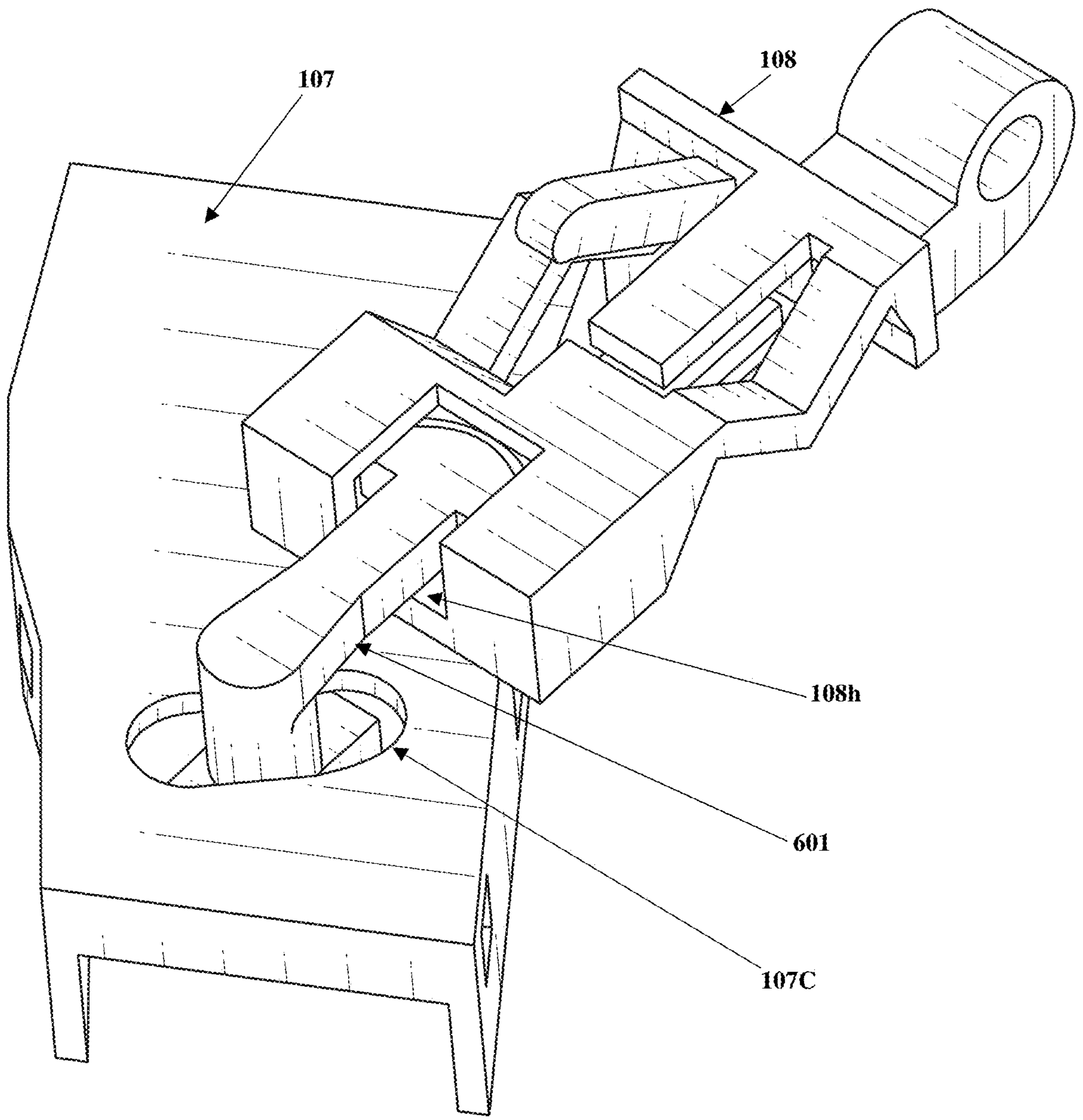
FIGS. 11A-11E illustrate the rotation of the bottom bite plate about the circumduction anchor rod when the circumduction anchor rod is connected to the bottom bite plate and the hinge plate.
Figure 11B:
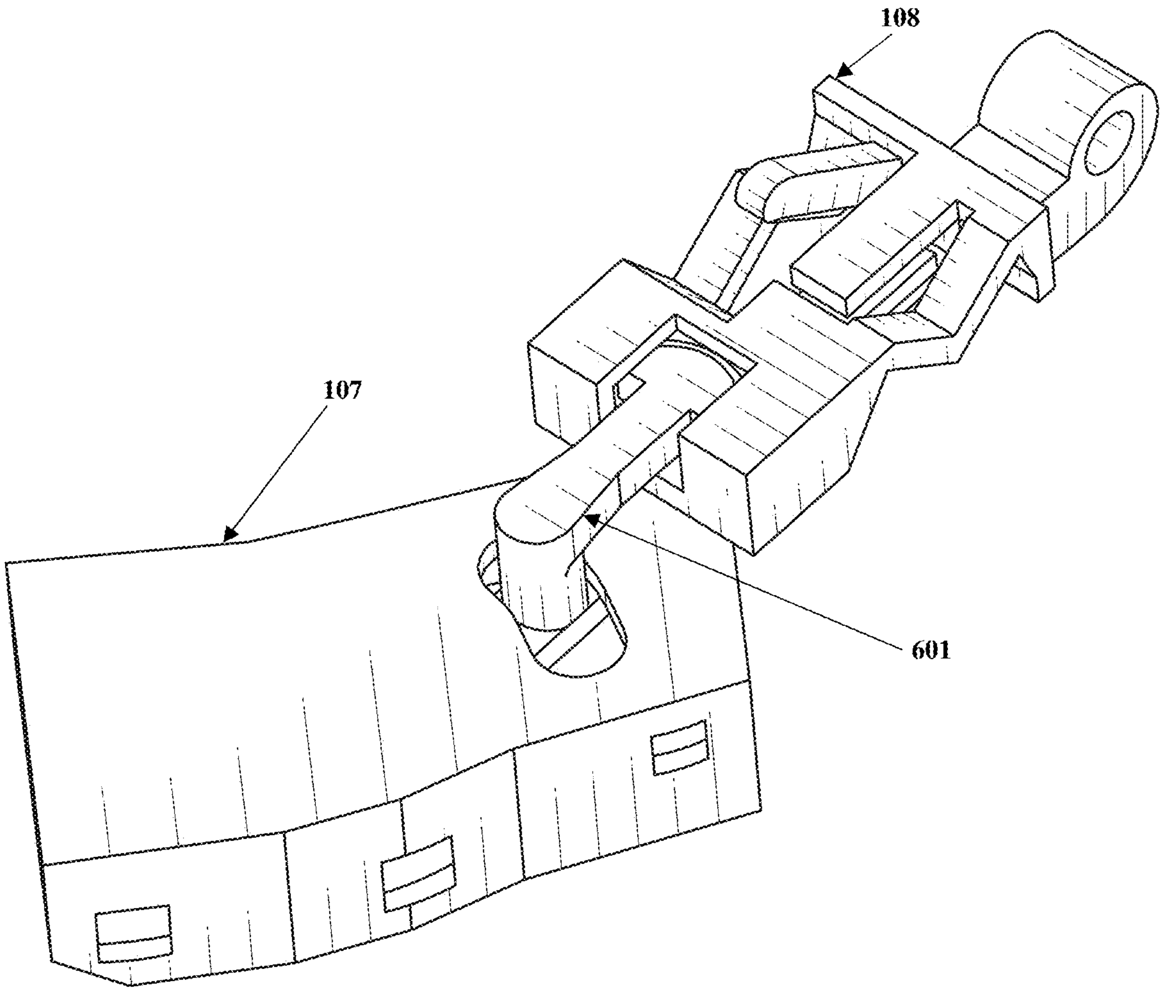
Figure 11C:
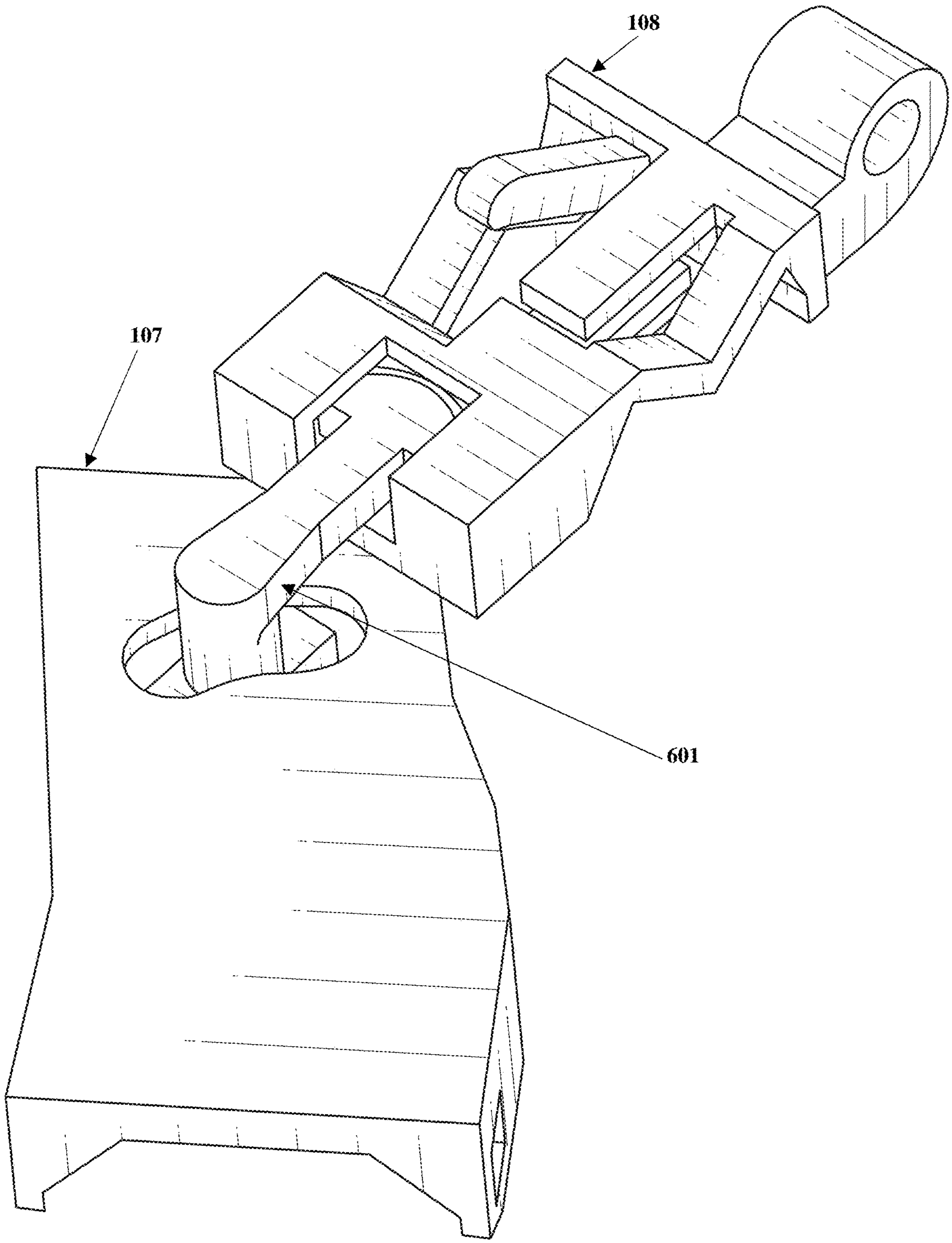
Figure 11D:
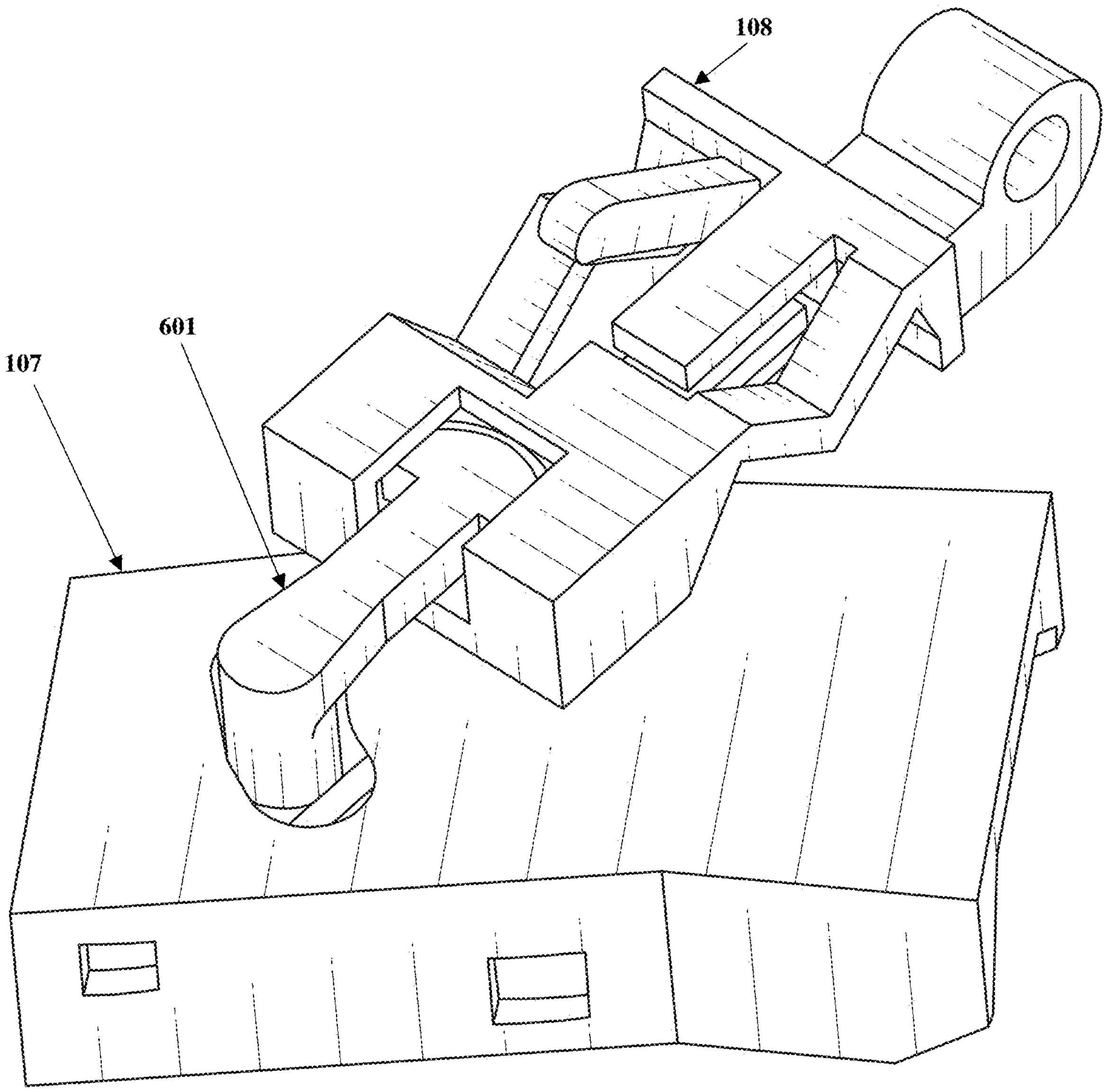
Figure 11E:
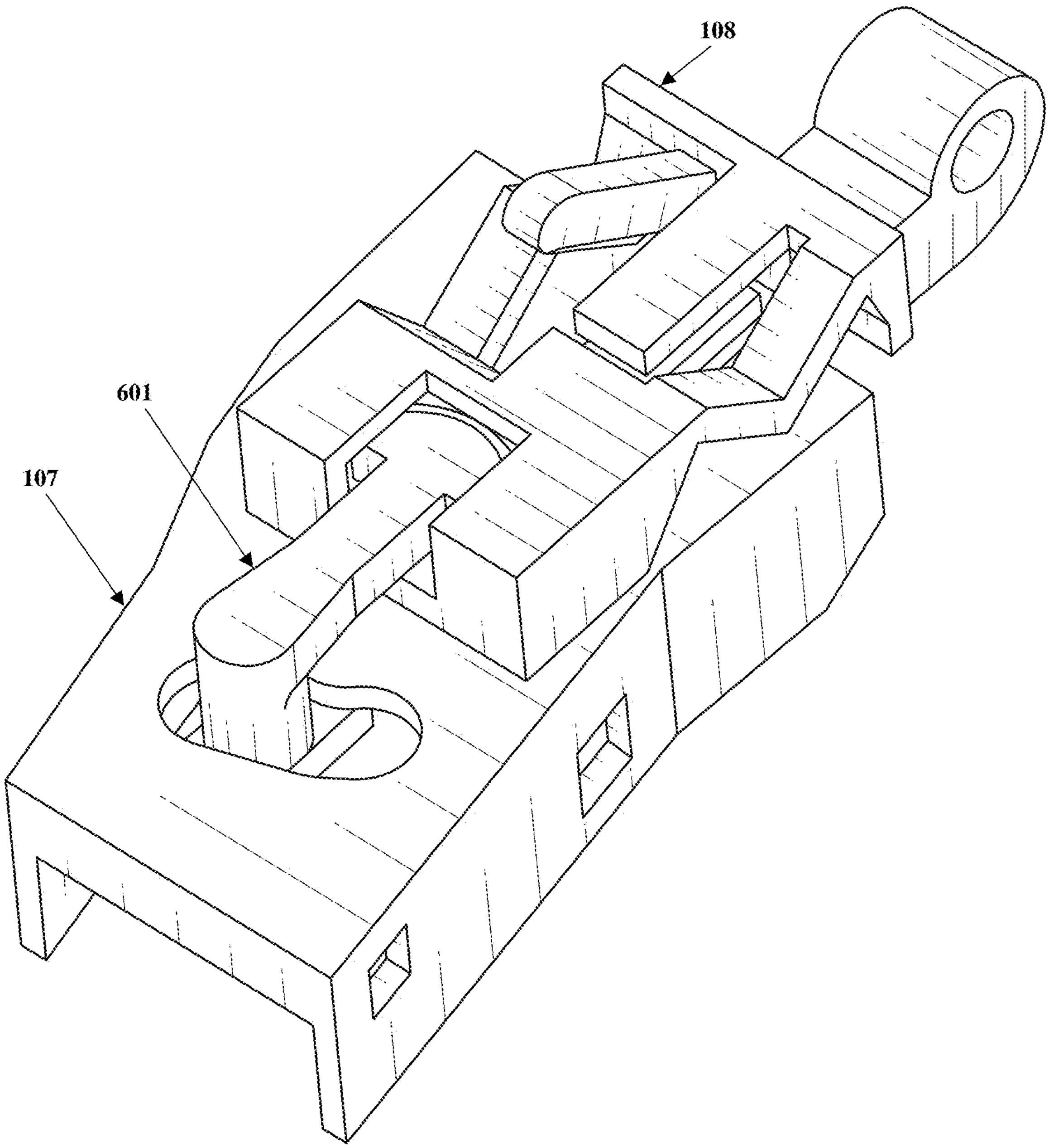

FIGS. 11A-11E illustrate the rotation of the bottom bite plate 107 about the circumduction anchor rod 601 when the circumduction anchor rod 601 is connected to the bottom bite plate 107 and the hinge plate 108. The bottom bite plate 107 can undergo a full circular rotation about the circumduction anchor rod 601 allowing for rotation of the mandible while the mandibular advancement device (MAD) 100 is in use. FIG. 11E illustrates a position of the bottom bite plate 107 relative to the hinge plate 108 with the bottom bite plate 107 aligned lengthwise along the length of the hinge plate 108, and the bottom bite plate front section 107*d* near the anchor hinge receptacle 108*h* and the bottom bite plate back section 107*e* near the second part 108*a* of the two parts of the hinge pin receptacle 110. This is the relative positioning of the bottom bite plate 107 and the hinge plate 108 in the left and the right bite tray assemblies when the MAD 100 is fitted to the mouth of a user of the MAD 100 using the fit connector 101.

Figure 12A:
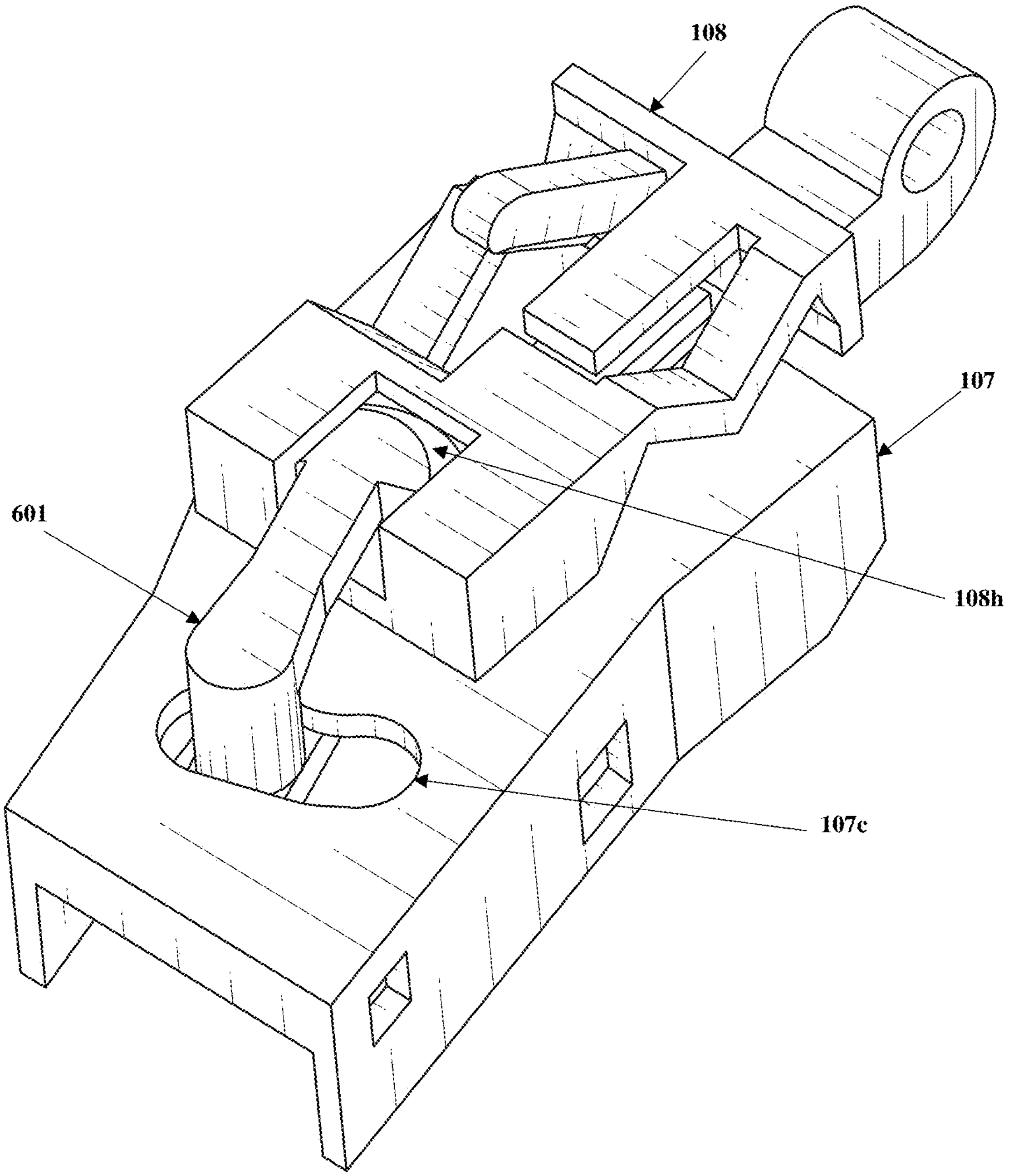
FIGS. 12A-12B illustrate lateral translation between the hinge plate and the bottom bite plate when the circumduction anchor rod is connected to the bottom bite plate and the hinge plate.
Figure 12B:
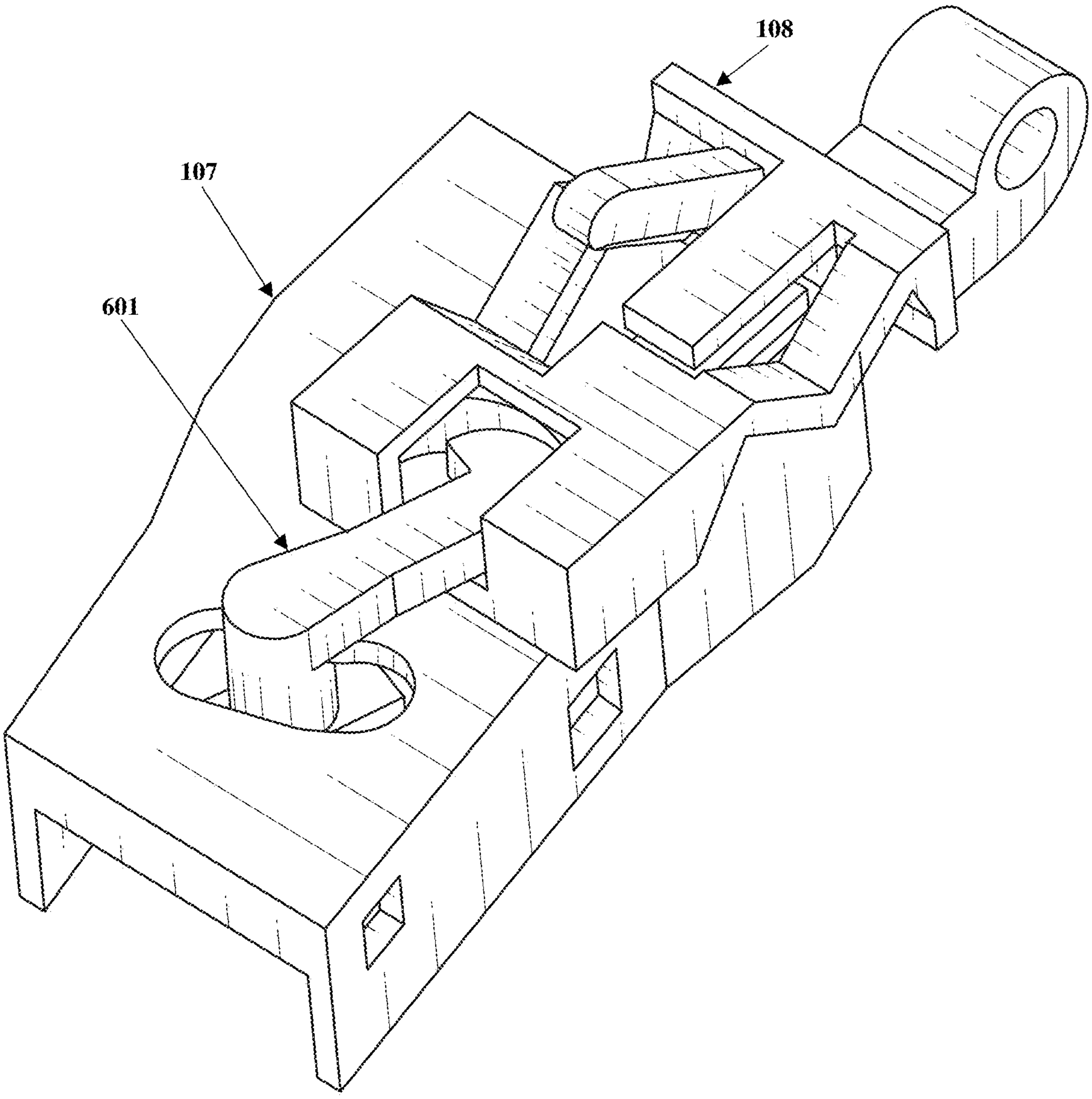

FIGS. 12A-12B illustrate lateral translation between the hinge plate 108 and the bottom bite plate 107 when the circumduction anchor rod 601 is connected to the bottom bite plate 107 and the hinge plate 108. The bottom bite plate 107 can move left and right with respect to the hinge plate 108. The anchor rod bottom section 601*a* of the circumduction anchor rod 601 translates within the anchor bottom receptacle 107*c* of the bottom bite plate 107. At the same time, the anchor rod front section 601*d* of the circumduction anchor rod 601 moves within the anchor hinge receptacle 108*h* of the hinge plate 108. During this articulation, the circumduction anchor rod 601 remains securely attached to both the bottom bite plate 107 and the hinge plate 108 as disclosed in the detailed description of FIGS. 2A-2B and 3A-3B.

Figure 13A:
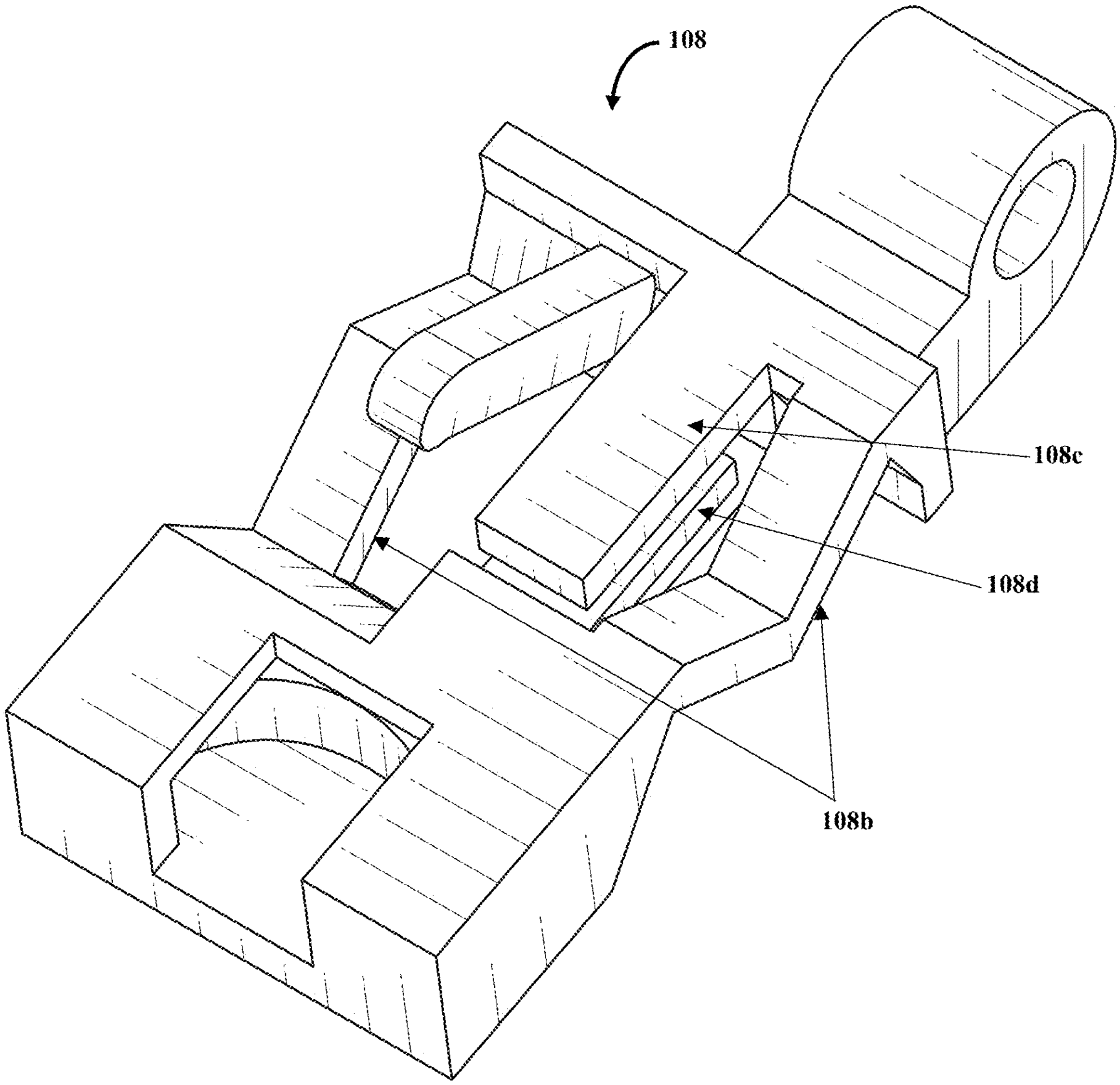
FIGS. 13A-13D illustrate protrusion and retraction of the hinge plate.
Figure 13B:
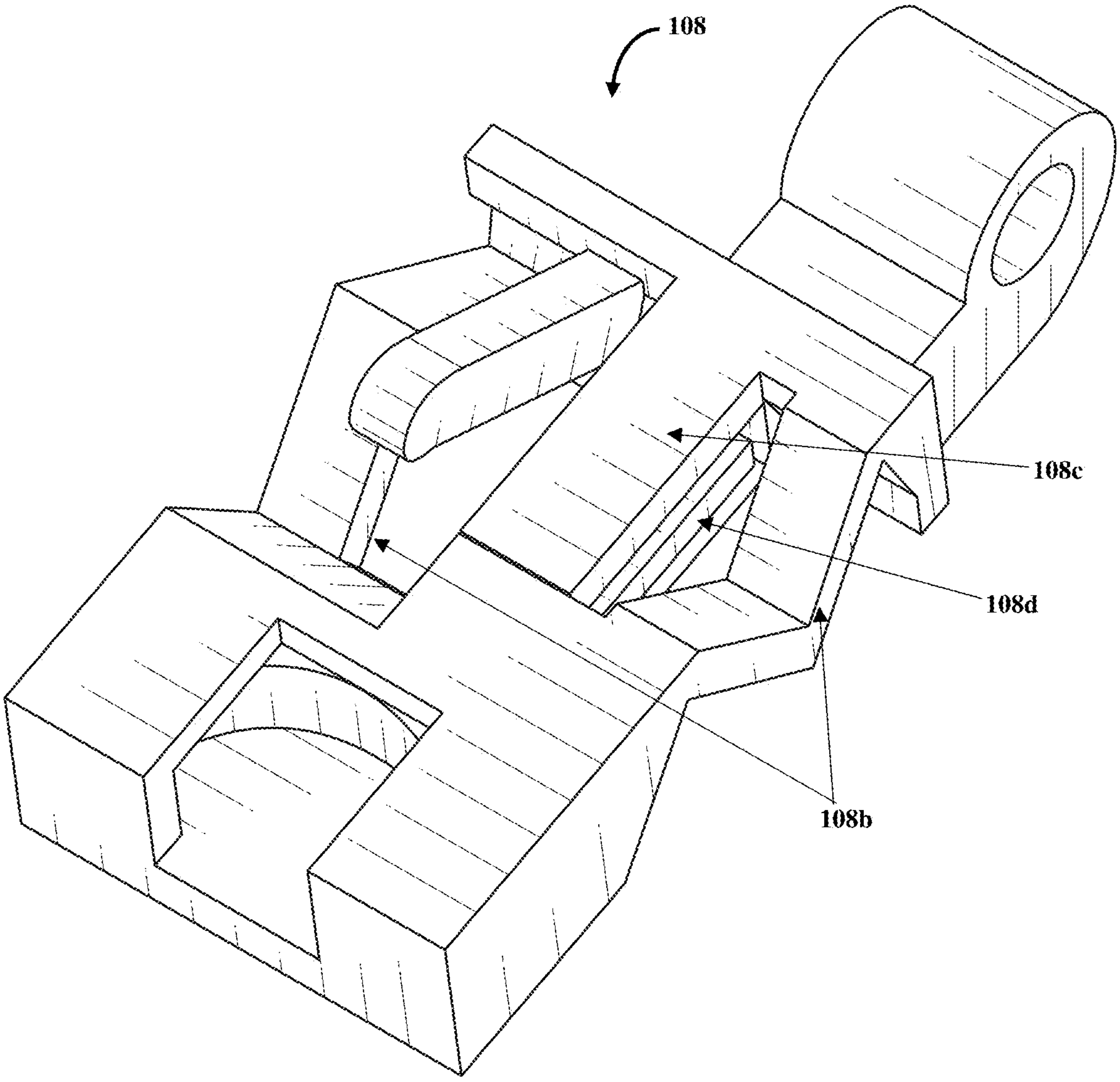
Figure 13C:
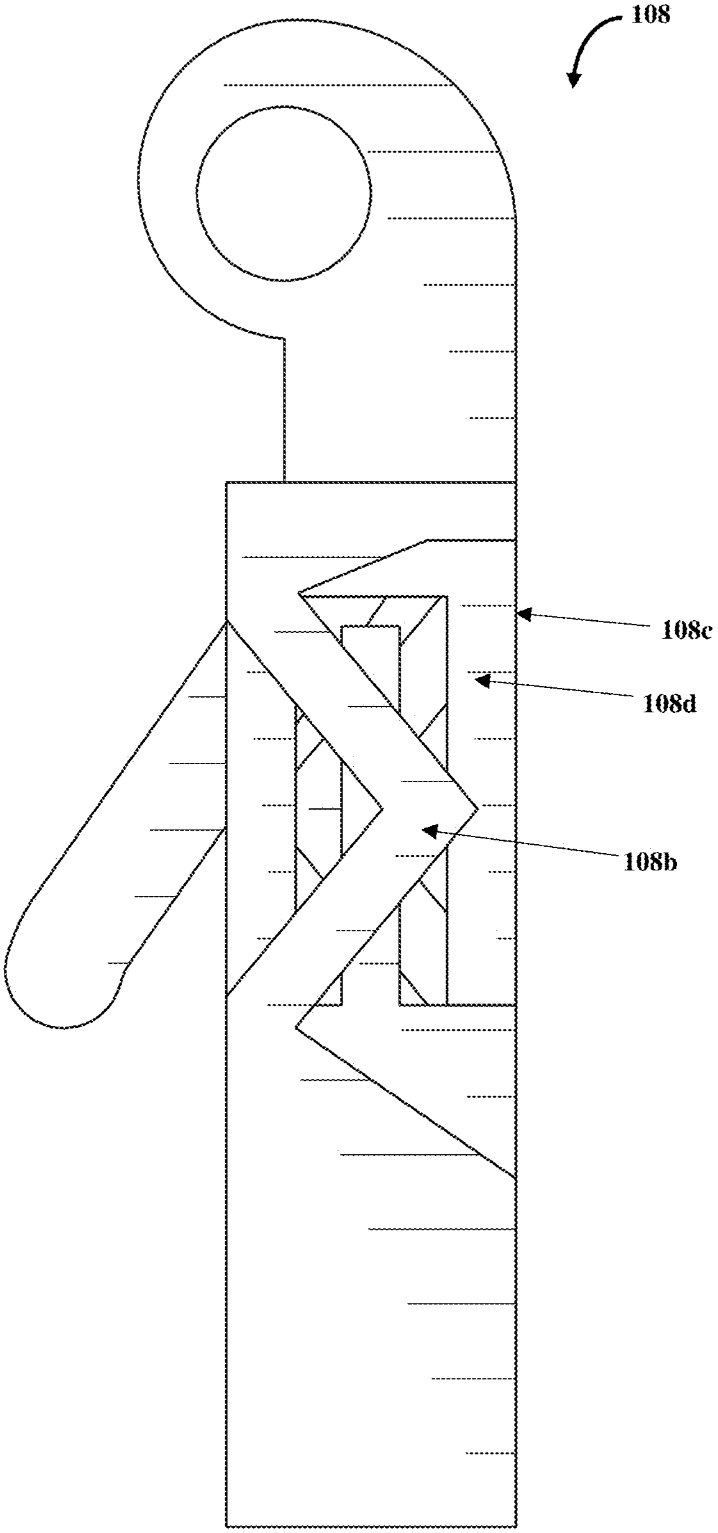
Figure 13D:
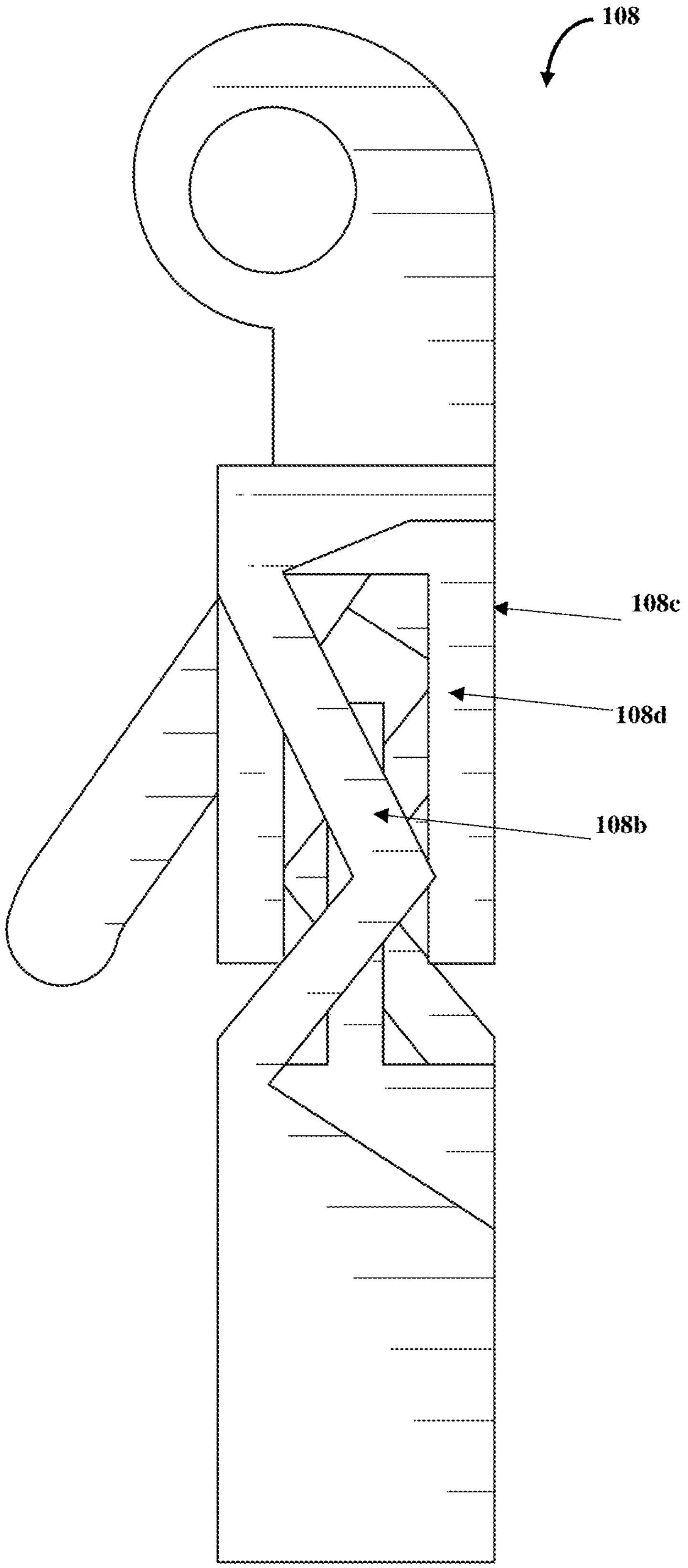

FIGS. 13A-13D illustrate protrusion and retraction of the hinge plate 108. FIGS. 13A-13B illustrate the perspective views and FIGS. 13C-13D illustrate the side views of the hinge plate 108. FIGS. 13A and 13C illustrate the position of the hinge plate 108 in the mandibular advancement device (MAD) 100 in use in the mouth of a user of the MAD 100 when the mouth is opened. The flexible member 108*b* extends to facilitate the protrusion of the mandible when the mouth is opened. FIGS. 13B and 13D illustrate the position of the hinge plate 108 in the MAD 100 when the mouth of the user is closed. The flexible member 108*b* contracts to facilitate the retraction of the mandible when the mouth is closed while the rectangular segments 108*d*, 108*i* and 108*j* in the dentate member 108*c* limit the contraction, maintaining a minimum advancement of the mandible.

Figure 14A:
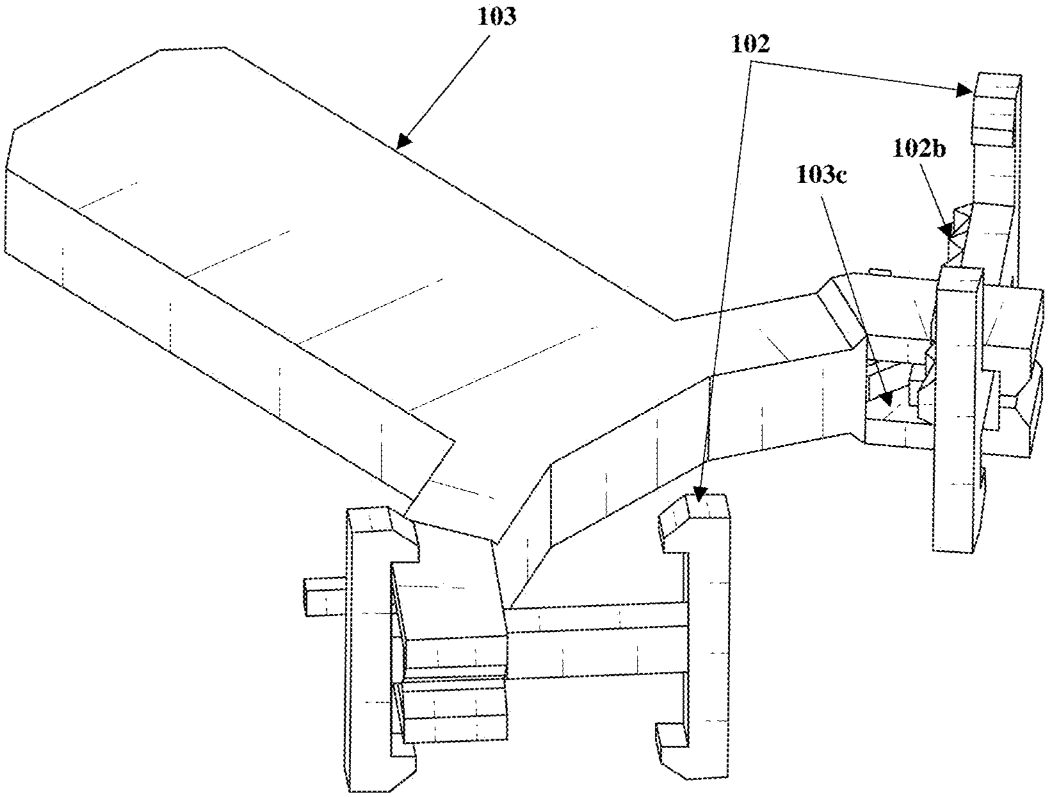
FIGS. 14A-14B illustrate the articulation between the H connectors and the Y connector.
Figure 14B:
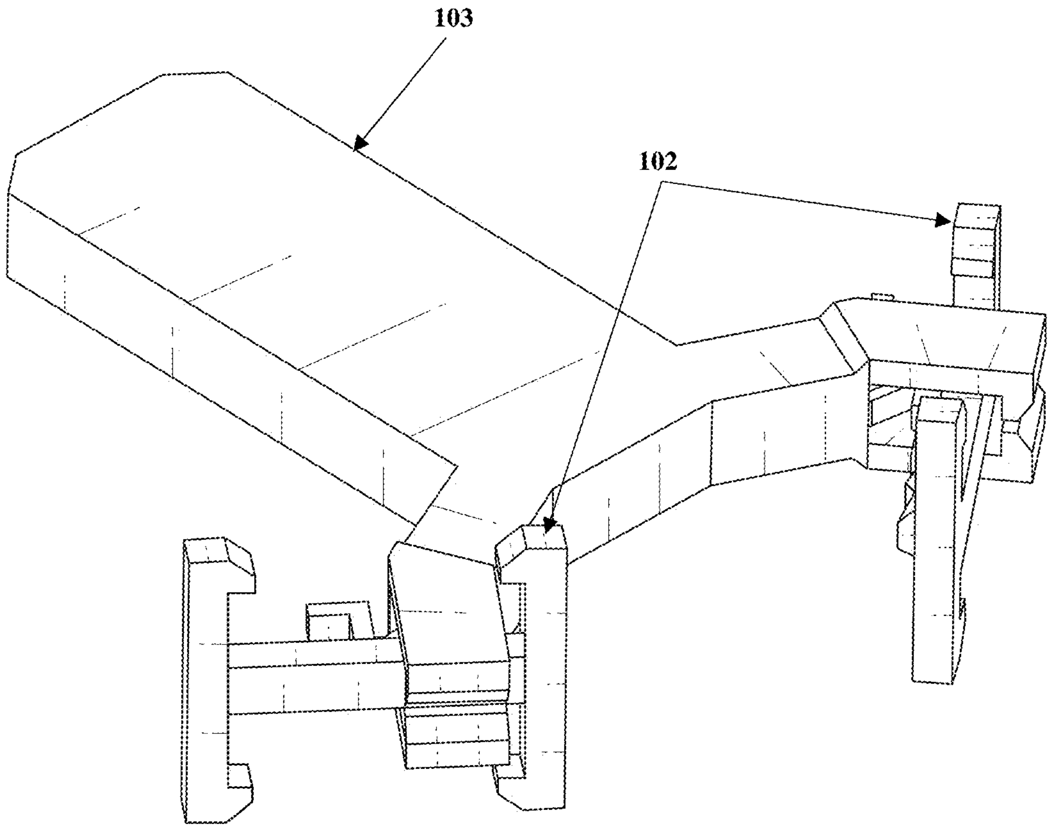

FIGS. 14A-14B illustrate the articulation between the H connectors and the Y connector. The crossbar 102*e* with the zigzag track 102*b* in each of the H connectors 102 is placed in the guide slot 103*d* in each arm 103*a* and 103*b* of the Y connector 103. The zigzag track 102*b* can be slid along the guide slot 103*d* to adjust the relative positioning of the H connectors 102 and the Y connector 103 while achieving a secure connection at each position as disclosed in the detailed description of FIGS. 8A-8B. The articulation facilitates adjustment of the fit connector 101 to the width of the mouth of a user of the mandibular advancement device (MAD) 100 when the MAD 100 is being fitted in the mouth of a user as disclosed in the detailed description of FIG. 1.

Figure 15:
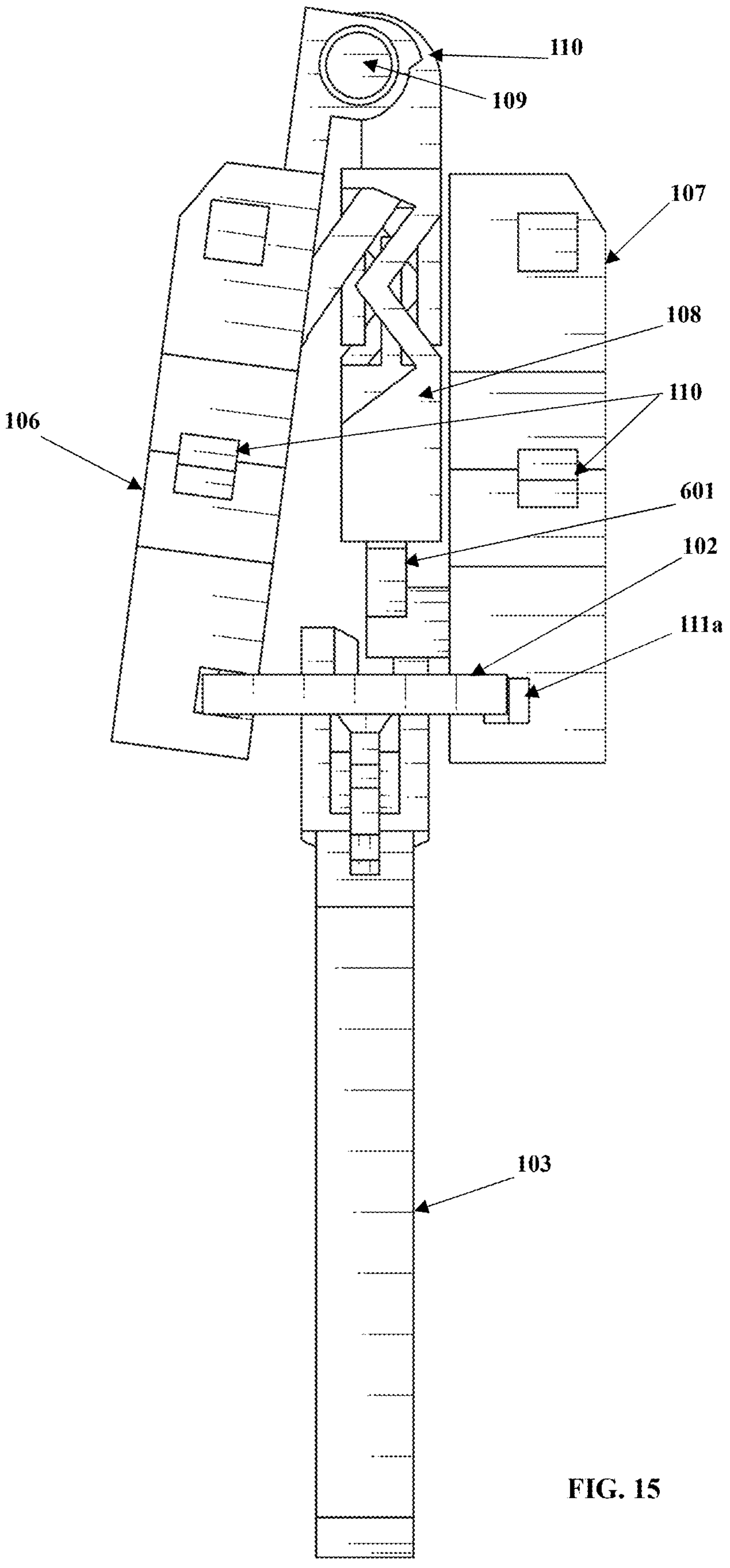
FIG. 15 illustrate a side view of the mandibular advancement device.

FIG. 15 illustrates a side view of the mandibular advancement device. The Y connector 103, one of the H connectors 102, the right bite tray assembly 105, the top bite plate 106, the hinge plate 108, the bottom bite plate 107, the pin 109, and the circumduction anchor rod 601 are disclosed in the detailed description of FIGS. 1-8C. One of the H connectors 102 is connected to the Y connector 103 through the guide slot 103*d* comprising the lock lever 103*f*. The H connector 102 is connected to the frontmost apertures 111*a* among the apertures 111 on the top bite plate 106 and the bottom bite plate 107 to attach the right bite tray assembly 105 to the H connector 102. The top bite plate 106 is connected to the hinge plate 108 via the pin 109 through the first part 106*c* and the second part 108*a* of the two parts of the hinge pin receptacle 110. The bottom bite plate 107 is connected to the hinge plate 108 via the circumduction anchor rod 601.

The tension prong 108*g* in the hinge plate 108 rests against the top bite plate 106, providing tension in the articulation between the top bite plate 106 and hinge plate 108 during the opening and closing of the mouth of the user of the mandibular advancement device (MAD) 100. The flexible member 108*b* facilitates protrusion and retraction of the hinge plate 108 when the mouth is opened and closed respectively by the user while the dentate member 108*c* maintains a minimum advancement of the mandible.

Figure 16A:
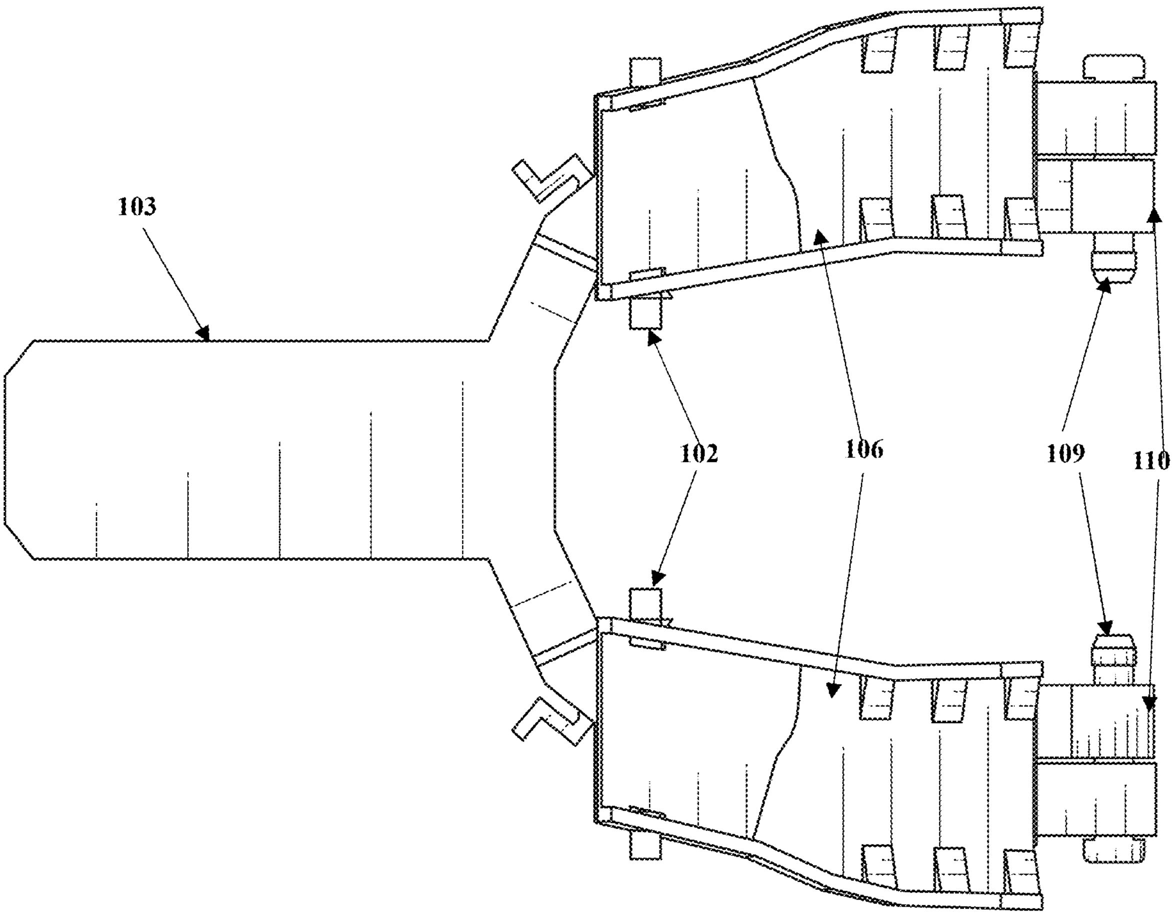
FIG. 16A illustrate a top view of the mandibular advancement device without a moldable bite insert in place.

FIG. 16A illustrates a top view of the mandibular advancement device without a moldable bite insert 1601 in place. The Y connector 103, the H connectors 102, the left bite tray assembly 104, the right bite tray assembly 105, the top bite plate 106 in each of the left and the right bite tray assemblies 104 and 105, the anchor hinge receptacle 108*h* of the hinge plate 108, and the pin 109 are as disclosed in the detailed description of FIGS. 1-8C.

Figure 16B:
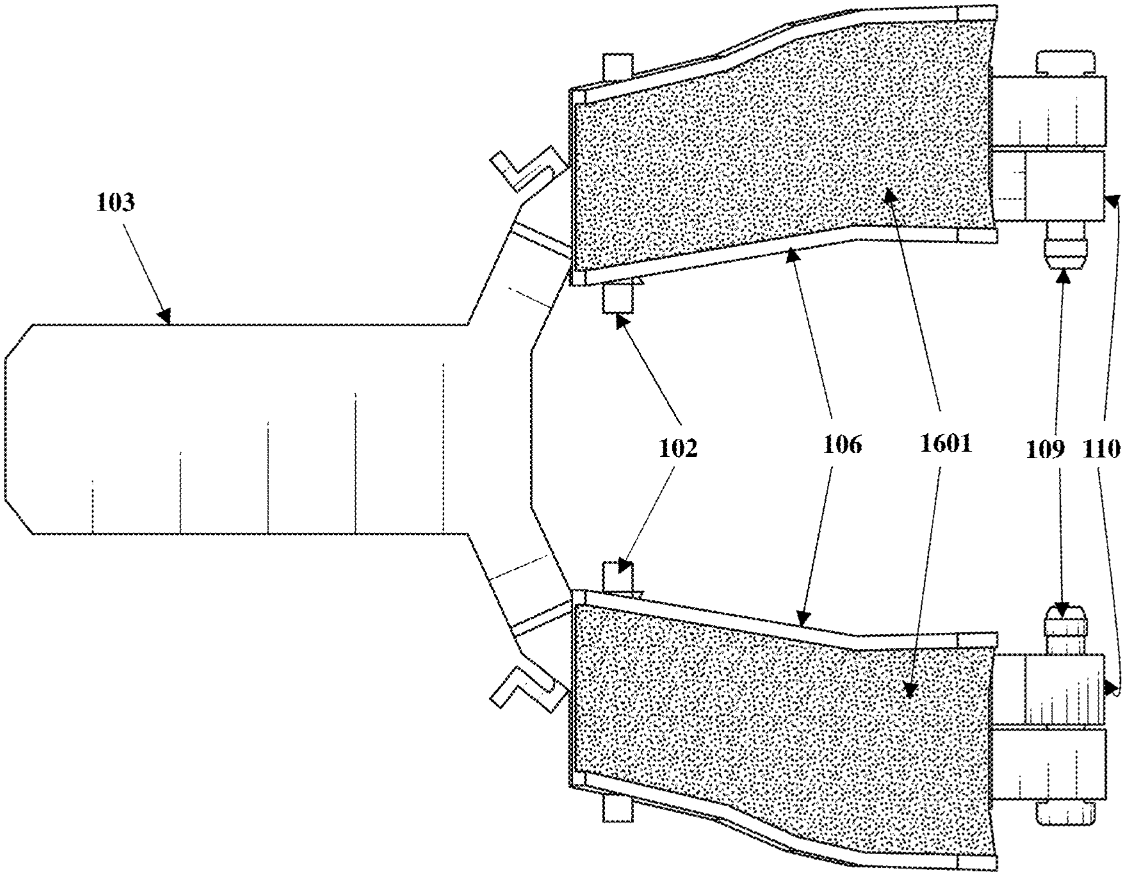
FIG. 16B illustrate a top view of the mandibular advancement device with a moldable bite insert in place.

FIG. 16B illustrates a top view of the mandibular advancement device 100 with a moldable bite insert 1601 in place. A moldable bite insert 1601 each is attached securely in the top enclosure 106*a* of the top bite plate 106 and in the bottom enclosure 107*a* of the bottom bite plate 107 of each of the left and the right bite tray assemblies 104 and 105 by fitting protrusions in each moldable bite insert 1601 into some of the apertures 111 in the top connector section 106*b* and the bottom connector section 107*b* respectively as disclosed in the detailed description of FIG. 1. The MAD 100 is fully assembled.

Figure 17:
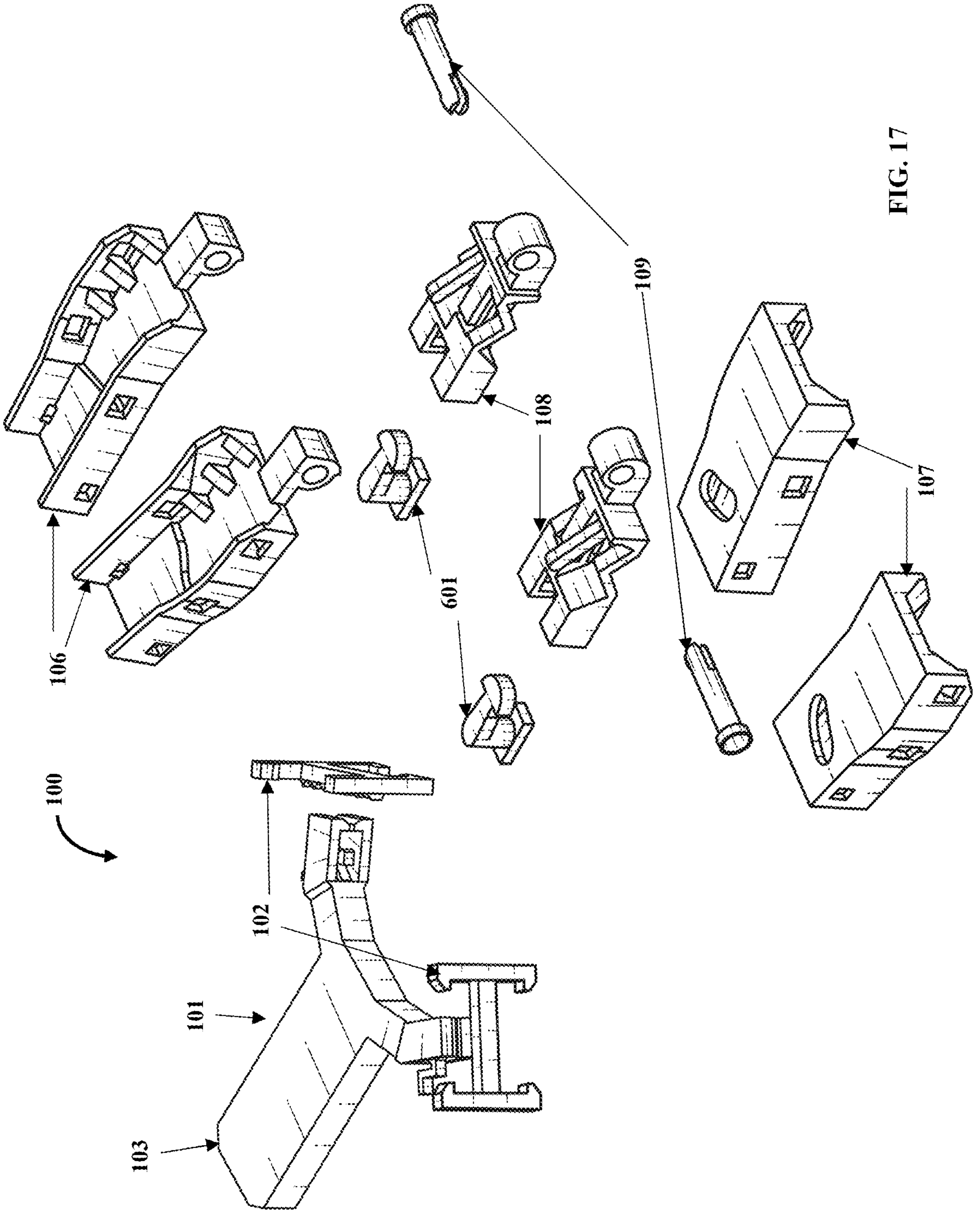
FIG. 17 illustrate an exploded view of the mandibular advancement device.

FIG. 17 illustrates an exploded view of the mandibular advancement device 100. The fit connector 101, the H connectors 102, the Y connector 103, the top bite plate 106, the hinge plate 108, the bottom bite plate 107, the pin 109, and the circumduction anchor rod 601 are disclosed in the detailed description of FIGS. 1-8C. Each of the H connectors 102 is attached in the guide slot 103*d* on one of the arms 103*a* and 103*b* of the Y connector 103, with each of the arms 103*a* and 103*b* receiving one of the H connectors 102. The top bite plate 106 is connected to the hinge plate 108 using the pin 109, which passes through the two parts of the hinge pin receptacle 110, namely, the first part 106*c* in the top bite plate 106 and the second part 108*a* in the hinge plate 108. The hinge plate 108 is to be connected to the bottom bite plate 107 using the circumduction anchor rod 601, which articulates with the hinge plate 108 in the anchor hinge receptacle 108*h* and with the bottom bite plate 107 in the anchor bottom receptacle 107*c*. The assembled left and right bite tray assemblies 104 and 105 are attached to the H connectors 102, wherein each prong 102*d* on each of the H connectors 102 occupies one of the frontmost apertures 111*a* in the top and the bottom bite plates, one prong 102*d* in one aperture.

The left bite tray assembly 104 and the right bite tray assembly 105 are each assembled from the top bite plate 106, the hinge plate 108, the bottom bite plate 107, the pin 109, and the neutral embodiment of the circumduction anchor rod 601. The H connectors 102 are then attached to the left bite tray assembly 104 and the right bite tray assembly 105 as disclosed in the detailed description of FIGS. 7A-7B, and to the Y connector 103, disclosed in the detailed description of FIGS. 8A-8B. The mandibular advancement device (MAD) 100 is fitted in the mouth of a user by holding the Y connector 103 by its stem 103*c* and adjusting the H connectors 102 to the width of the mouth to fit the MAD 100 in the mouth, whereby movement of the left and the right bite tray assemblies 104 and 105 are prevented. Thereafter, the MAD 100 is removed from the mouth and heated in boiling water to ready the moldable bite inserts in the top bite plates 106 and the bottom bite plates 107 in the left and the right bite tray assemblies 104 and 105 for obtaining a dental impression. The MAD 100 is then placed again in the mouth of the user using the stem 103*c* of the Y connector 103 to procure a dental impression simultaneously in each of the moldable bite inserts, wherein the connection between the H connectors 102 and the left and the right bite tray assemblies 104 and 105 prevents any movement of the MAD 100.

With the moldable bite inserts 1601 molded to conform to the portion of the upper teeth and the portion of the lower teeth around which the top bite plate 106 and the bottom bite plate 107 respectively fit, a stable and comfortable fit is ensured for the MAD 100 in the mouth of the user. The fit connector 101 is then detached from the left and the right bite tray assemblies 104 and 105, which are thereafter used independently without the fit connector 101 by the user. The user can adjust the level of mandibular advancement by replacing the neutral embodiment of the circumduction anchor rod 601 with another embodiment of desired length.

While the mandibular advancement device (MAD) 100 is advancing the mandible, the articulation between the top bite plate 106 and the hinge plate 108 facilitates up and down movement of the mandible. The flexible member 108*b* of the hinge plate 108 facilitates protrusion and retraction of the mandible. These two articulations together mimic the open-protrude and close-retract motion of the mandible. The articulation between the hinge plate 108 and the circumduction anchor rod 601 facilitates side-to-side translation of the mandible and the articulation between the circumduction anchor rod 601 and the bottom bite plate 107 facilitates side-to-side translation and rotation of the mandible. These two articulations together mimic the translation-rotation movement of the mandible. Both the sets of movements together facilitate circumduction of the MAD 100, which mimics the circumduction of the mandible.

In an embodiment of the mandibular advancement device (MAD) 100, the MAD 100 comprises a left and a right mirrored top bite plate 106, a left and a right mirrored bottom bite plate 107, two left and two right mirrored moldable bite inserts, a left and a right mirrored hinge plate, eight circumduction anchor rods 601 comprising a set of two circumduction anchor rods 601 in four different sizes, two pins 109, and a Y connector 103 and two H connectors 102 as part of the fit connector 101.

The top bite plate 106 has left and right iterations, which have the same measurements, and are mirror versions of each other. The top bite plate 106 is 38.2 mm long with the top bite plate front section 106*d* measuring 30 mm and the top bite plate back section 106*e* measuring 8.2 mm. The top enclosure 106*a* is 2 mm thick in the top bite plate front section 106*d* and 1 mm thick in the top bite plate back section 106*e* with the top enclosure shoulder 106*f* separating the two sections. The top bite plate 106 is 14 mm wide at the top bite plate front section 106*d* and widens to 17 mm at the top bite plate back section 106*e*. The top connector section 106*b* comprises 7 mm tall and 1 mm thick walls on both sides of the top bite plate 106 that run the length of the top bite plate 106. The walls have the apertures 111 with the frontmost apertures 111*a* being smaller and used for attachment to the H connectors 102. The remaining apertures 111 are made to fit the protrusions of the moldable bite insert.

The bottom bite plate 107 has left and right iterations, which have the same measurements, and are mirror images of each other. The bottom bite plate 107 is 30 mm long and is 14 mm wide at the bottom bite plate front section 107*d* and widens to 17 mm at the bottom bite plate back section 107*e*. The bottom enclosure 107*a* is 3 mm thick at the bottom bite plate front section 107*d* and 2 mm thick at the bottom bite plate back section 107*e* with a bottom enclosure shoulder 107*f* separating the two sections. The bottom bite plate 107 has 7 mm tall and 1 mm thick walls on both sides of the bottom bite plate 107 that run the length of the bottom bite plate 107. The walls have the apertures 111 with the frontmost apertures 111*a* being smaller and used for attachment to the H connectors 102. The remaining apertures 111 are made to fit the protrusions on the moldable bite insert. The bottom enclosure 107*a* has the anchor bottom receptacle 107*c*, with an entry hole smaller than the receptacle itself, at the bottom bite plate front section 107*d*.

The moldable bite insert has a left and a right iteration configured to fit inside both the top bite plate 106 and the bottom bite plate 107. It is 30 mm long and is 10 mm wide at the front, widening to 13 mm at the back. It has walls that are 5.5 mm tall at the front and 6.5 mm tall at the back. The walls are 3 mm thick and have three pegs, each measuring 2.5 mm in length, 2.5 mm in width, and 1 mm in thickness, along their length. The floor of the moldable bite insert is 2 mm thick at the front and 3 mm thick at the back to adjust to the varied thickness between the front and back sections of the top and bottom bite plate enclosures.

The circumduction anchor rods 601 are eight in number, are of four different sizes, and are to be used in pairs. The anchor rod bottom section 601*a*, the anchor rod front section 601*d*, and the anchor rod post 601*b* are the same for all the sizes with the only difference between the different sized rods being the length of the anchor rod middle section 601*c*. The neutral embodiment of the circumduction anchor rod 601 has the following measurements. The anchor rod post 601*b* is 3.5 mm in diameter and 5 mm in height. The anchor rod bottom section 601*a* is 7 mm long, 3.5 mm wide, and 1.5 mm thick. The top of the anchor rod post 601*b* bends and forms into a 7.5 mm long, 2.5 mm wide, and 2 mm thick anchor rod middle section 601*c*. The anchor rod middle section 601*c* ends in a semicircle of diameter 5.7 mm and thickness 2.5 mm. All the measurements except the length of the anchor rod middle section 601*c* are the same for the other embodiments of the circumduction anchor rod 601. The lengths of the anchor rod middle section 601*c* for the other embodiments are 4.5 mm, 7 mm, and 9.5 mm.

The hinge plate 108 has left and right iterations that are mirror images of each other. It is 27 mm long and 12 mm wide. It has a front and a back section. The back section measures 6.25 mm in length, 8 mm in width, and 5 mm in height, and houses a 3 mm diameter hole for the second part 108*a* of the two parts of the hinge pin receptacle 110 through which the pin 109 is inserted. The front section measures 19 mm in length, 12 mm in width, and 5 mm in height. It houses the flexible member 108*b*, which extends under tension and shortens under compression. Moreover, it houses the dentate member 108*c*, which both resist torsional forces and limit the amount of retraction of the hinge plate 108 under compression so that mandibular advancement is always achieved even under a high compressive force. The front section of the hinge plate 108 also houses the tension prong 108*g*, which measures 7 mm in length, 1.5 mm in width, and 1.5 mm in thickness. The tension prong 108*g* provides slight passive opening pressure to help with the fit of the mandibular advancement device (MAD) 100 while in use. The front of the front section has the anchor hinge receptacle 108*h*, which is meant to articulate with the anchor rod front section 601*d*. The anchor hinge receptacle 108*h* has an opening that is smaller than the receptacle itself.

The pin 109 has a length of 15.5 mm with a main shaft of 2.8 mm diameter. The head 109*a* has a diameter of 3.8 mm and the split end 109*b* has a diameter of 3.2 mm.

The Y connector 103 is shaped as the capital letter Y and has guide slots 103*d* at the end of its arms 103*a* and 103*b* to attach the H connectors 102. The connection permits the sliding of the H connectors 102 along the guide slot 103*d* while firmly holding the H connectors 102 in place at a chosen position. The Y connector 103 also comprises the stem 103*c*.

The H connectors 102 are each shaped as the capital letter H and have a prong 102*d* each at the four terminal points of the vertical strokes 102*a* to attach to the top and the bottom bite plates. The crossbar 102*e* with the zigzag track 102*b* can be slid along the guide slot 103*d* in each arm 103*a* and 103*b* of the Y connector 103.

The foregoing examples have been provided merely for explanation and are in no way to be construed as limiting of the mandibular advancement device (MAD) 100 disclosed herein. While the MAD 100 has been described with reference to various embodiments, it is understood that the words, which have been used herein, are words of description and illustration, rather than words of limitation. Furthermore, the dimensions of parts described in different embodiments of the MAD 100 are exemplary and are not intended to be limited to the dimensions disclosed herein. Furthermore, although the MAD 100 has been described herein with reference to particular means, materials, and embodiments, the MAD 100 is not intended to be limited to the particulars disclosed herein; rather, the MAD 100 extends to all functionally equivalent structures, methods and uses, such as are within the scope of the appended claims. While multiple embodiments are disclosed, it will be understood by those skilled in the art, having the benefit of the teachings of this specification, that the MAD 100 disclosed herein are capable of modifications and other embodiments may be effected and changes may be made thereto, without departing from the scope and spirit of the MAD 100 disclosed herein.

I claim:

1. A mandibular advancement device for facilitating a protrusion, a retraction, a lateral translation, and a rotation of a mandible while advancing the mandible, the mandibular advancement device comprising:

a fit connector;

a left bite tray assembly and a right bite tray assembly, wherein each of the left and the right bite tray assemblies comprise:

a top bite plate configured to fit around a portion of the upper teeth of a user of the mandibular advancement device, the top bite plate comprising a top enclosure for a moldable bite insert, a top connector section, and a first part of two parts of a hinge pin receptacle;

a bottom bite plate configured to fit around a portion of the lower teeth of the user, the bottom bite plate comprising a bottom enclosure for a moldable bite insert, a bottom connector section, and an anchor bottom receptacle;

a hinge plate detachably interposed between the top bite plate and the bottom bite plate, the hinge plate comprising a flexible member, a dentate member, a tension prong, a second part of the two parts of the hinge pin receptacle, and an anchor hinge receptacle, wherein the flexible member facilitates the protrusion and the lateral retraction of the mandible and the dentate member maintains a minimum advancement of the mandible;

a pin for operably connecting the hinge plate to the top bite plate via the hinge pin receptacle, wherein the operable connection facilitates opening and closing of the mandible; and a circumduction anchor rod for operably connecting the hinge plate to the bottom bite plate via the anchor hinge receptacle and the anchor bottom receptacle, wherein the operable connection facilitates the lateral translation and the rotation of the mandible, thereby facilitating the protrusion, the retraction, the lateral translation, and the rotation of the mandible while advancing the mandible; and the fit connector comprising a Y connector with two arms and a pair of H connectors, wherein each of the pair of H connectors is detachably attached to an arm of the Y connector, and the top bite plate and the bottom bite plate of one of the left bite tray assembly and the right bite tray assembly for procuring a dental impression simultaneously in each of the moldable bite inserts in the top bite plates and the bottom bite plates in the left and the right bite tray assemblies.

2. The mandibular advancement device of claim 1, wherein the top connector section of the top bite plate and the bottom connector section of the bottom bite plate comprise apertures for detachably attaching the top bite plate and the bottom bite plate respectively to one of the pair of H connectors and for attaching the moldable bite insert in each of the top enclosure of the top bite plate and the bottom enclosure of the bottom bite plate.

3. The mandibular advancement device of claim 2, wherein the moldable bite inserts have protrusions that fit into the apertures in the top connector section of the top bite plate and the bottom connector section of the bottom bite plate for stably fitting the mandibular advancement device around the teeth of the user.

4. The mandibular advancement device of claim 1, wherein each of the pair of H connectors has a prong at each four terminal points of a vertical strokes of a capital letter H for detachably attaching the pair of H connectors to the top bite plate and the bottom bite plate of one of the left bite tray assembly and the right bite tray assembly.

5. The mandibular advancement device of claim 4, wherein the detachable attachment of each of the pair of H connectors to an arm of the Y connector facilitates:

a side to side movement of the H connectors to accommodate mouths of different widths for fitting the mandibular advancement device in the mouth; and stabilizing and arresting movement of the top bite plate and the bottom bite plate to further ensure accurate dental impressions in each of the moldable bite inserts in the top bite plates and the bottom bite plates in the left and the right bite tray assemblies.

6. The mandibular advancement device of claim 1, wherein the top bite plate, the bottom bite plate, and the hinge plate of the right bite tray assembly are laterally inverted mirror images of the top bite plate, the bottom bite plate, and the hinge plate respectively of the left bite tray assembly.

7. The mandibular advancement device of claim 1, wherein the flexible member in the hinge plate extends and contracts for the protrusion and the retraction that accompany opening and closing of the mouth respectively of the user.

8. The mandibular advancement device of claim 1, wherein the dentate member in the hinge plate maintains the minimum advancement of the mandible during the retraction of the mandible.

9. The mandibular advancement device of claim 1, wherein the anchor hinge receptacle and the anchor bottom receptacle provide room for the circumduction anchor rod to rotate with the mandible and the anchor bottom receptacle is wide to allow the circumduction anchor rod to laterally translate with sidewards movement of the mandible.

10. The mandibular advancement device of claim 1, wherein the circumduction anchor rod is of varying lengths available for replacement in the mandibular advancement device for providing different levels of mandibular advancement.

11. The mandibular advancement device of claim 1, wherein the tension prong in the hinge plate provides a tension when a user opens mouth for providing a stable fit of the mandibular advancement device in the mouth.

12. The mandibular advancement device of claim 1, wherein the fit connector is for fitting the mandibular advancement device to the mouth of the user for the first time for procuring a dental impression simultaneously in each of the moldable bite inserts in the top bite plates and the bottom bite plates in the left and the right bite tray assemblies without allowing movement of the mandibular advancement device, remaining detached from the left and the right bite tray assemblies thereafter.

13. A bite tray assembly of a mandibular advancement device, comprising:

a top bite plate configured to fit around a portion of the upper teeth of a user of the mandibular advancement device, the top bite plate comprising a top enclosure for a moldable bite insert, a top connector section, and a first part of two parts of a hinge pin receptacle;

a bottom bite plate configured to fit around a portion of the lower teeth of the user, the bottom bite plate comprising a bottom enclosure for a moldable bite insert, a bottom connector section, and an anchor bottom receptacle;

a hinge plate detachably interposed between the top bite plate and the bottom bite plate, the hinge plate comprising a flexible member, a dentate member, a tension prong, a second part of the two parts of the hinge pin receptacle, and an anchor hinge receptacle, wherein the flexible member facilitates a protrusion and a retraction of a mandible and the dentate member maintains a minimum advancement of the mandible;

a pin for operably connecting the hinge plate to the top bite plate via the hinge pin receptacle, wherein the operable connection facilitates opening and closing of the mandible; and a circumduction anchor rod for operably connecting the hinge plate to the bottom bite plate via the anchor hinge receptacle and the anchor bottom receptacle, wherein the operable connection facilitates a lateral translation and a rotation of the mandible, thereby facilitating the protrusion, the retraction, the lateral translation, and the rotation of the mandible while advancing the mandible.

14. The bite tray assembly of claim 13, wherein the top connector section of the top bite plate and the bottom connector section of the bottom bite plate comprise apertures for attaching the moldable bite insert in each of the top enclosure of the top bite plate and the bottom enclosure of the bottom bite plate respectively.

15. The bite tray assembly of claim 14, wherein the moldable bite inserts have protrusions that fit into the apertures in the top connector section of the top bite plate and the bottom connector section of the bottom bite plate for stably fitting the bite tray assembly around the teeth of the user.

16. The bite tray assembly of claim 13, wherein the top bite plate, the bottom bite plate, and the hinge plate of the right bite tray assembly are laterally inverted mirror images of the top bite plate, the bottom bite plate, and the hinge plate respectively of the left bite tray assembly.

17. The bite tray assembly of claim 13, wherein the flexible member in the hinge plate extends and contracts for the protrusion and the retraction that accompany opening and closing of a mouth respectively of the user.

18. The bite tray assembly of claim 13, wherein the dentate member in the hinge plate maintains the minimum advancement of the mandible during the retraction of the mandible.

19. The bite tray assembly of claim 13, wherein the anchor hinge receptacle and the anchor bottom receptacle provide room for the circumduction anchor rod to rotate with the mandible and the anchor bottom receptacle is wide to allow the circumduction anchor rod to laterally translate with sidewards movement of the mandible.

20. The bite tray assembly of claim 13, wherein the circumduction anchor rod is of varying lengths available for replacement in the mandibular advancement device for providing different levels of mandibular advancement.

21. The bite tray assembly of claim 13, wherein the tension prong in the hinge plate provides a tension when the user opens mouth for providing a stable fit of the mandibular advancement device in the mouth.

* * * * *